US006855410B2

(12) United States Patent
Buckley

(10) Patent No.: US 6,855,410 B2
(45) Date of Patent: Feb. 15, 2005

(54) PHASE CHANGE MATERIAL THERMAL CAPACITOR CLOTHING

(76) Inventor: Theresa M. Buckley, P.O. Box 1239, Ashton, MD (US) 20861

( * ) Notice: Subject to any disclaimer, the term of this patent is extended or adjusted under 35 U.S.C. 154(b) by 0 days.

(21) Appl. No.: 09/989,913

(22) Filed: Nov. 20, 2001

(65) Prior Publication Data

US 2002/0164473 A1 Nov. 7, 2002

Related U.S. Application Data

(63) Continuation of application No. 09/033,439, filed on Mar. 2, 1999, now Pat. No. 6,319,599, which is a continuation-in-part of application No. 08/404,419, filed on Mar. 15, 1995, now Pat. No. 5,722,482, which is a continuation-in-part of application No. 07/913,246, filed on Jul. 14, 1992, now Pat. No. 6,004,662.

(51) Int. Cl.⁷ .............................. B32B 5/18; B63C 11/04; A43B 5/04; A41D 1/02; A41D 1/06
(52) U.S. Cl. .............................. 428/311.11; 428/313.5; 428/316.6; 428/318.4; 428/320.2; 428/321.1; 428/321.5; 428/327.7; 428/411.1; 36/2 R; 36/117.1; 2/2.16; 2/93; 2/113; 2/115; 2/173; 2/200.1; 2/206; 2/209; 2/227
(58) Field of Search .............................. 36/117.1, 2 R; 428/311.11, 313.5, 316.6, 318.4, 320.2, 321.1, 321.5, 327.7, 411.1; 2/2.15, 2.16, 93, 173, 200.1, 206, 209, 227, 113, 115

(56) References Cited

U.S. PATENT DOCUMENTS

| 2,357,851 A | 9/1944 | Scheyer ............... 428/242 |
| 2,515,298 A | 7/1950 | Feldman |
| 3,032,772 A | 5/1962 | Fonash ............... 2/21 |

(List continued on next page.)

FOREIGN PATENT DOCUMENTS

| JP | 0101392 | 4/1990 |
| JP | 0213191 | 12/1993 |
| WO | WO 94/02257 | 2/1994 |

OTHER PUBLICATIONS

Vale et al., "Phase Change Materials Handbook", Sep. 1971, pp 7–1 to 7–3.

(List continued on next page.)

Primary Examiner—Ramsey Zacharia
(74) Attorney, Agent, or Firm—Foley & Lardner LLP

(57) ABSTRACT

An apparatus and method for metabolic cooling and insulation of a user in a cold environment. In its preferred embodiment the apparatus is a highly flexible composite material having a flexible matrix containing a phase change thermal storage material. The apparatus can be made to heat or cool the body or to act as a thermal buffer to protect the wearer from changing environmental conditions. The apparatus may also include an external thermal insulation layer and/or an internal thermal control layer to regulate the rate of heat exchange between the composite and the skin of the wearer. Other embodiments of the apparatus also provide 1) a path for evaporation or direct absorption of perspiration from the skin of the wearer for improved comfort and thermal control, 2) heat conductive pathways within the material for thermal equalization, 3) surface treatments for improved absorption or rejection of heat by the material, and 4) means for quickly regenerating the thermal storage capacity for reuse of the material. Applications of the composite materials are also described which take advantage of the composite's thermal characteristics. The examples described include a diver's wet suit, ski boot liners, thermal socks, gloves and a face mask for cold weather activities, and a metabolic heating or cooling blanket useful for treating hypothermia or fever patients in a medical setting and therapeutic heating or cooling orthopedic joint supports.

44 Claims, 8 Drawing Sheets

FIGURE 3

U.S. PATENT DOCUMENTS

| | | | |
|---|---|---|---|
| 3,536,058 A | * 10/1970 | Hearst et al. | 126/204 |
| 3,652,200 A | 3/1972 | Miyasaka | 8/54 |
| 3,674,027 A | 7/1972 | Fleischmajer | |
| 3,940,811 A | 3/1976 | Tomikawa et al. | 428/304.4 |
| 3,950,789 A | 4/1976 | Konz et al. | 2/93 |
| 3,969,551 A | * 7/1976 | Ellsworth | 427/282 |
| 4,003,426 A | 1/1977 | Best et al. | 165/104 |
| 4,055,699 A | 10/1977 | Hsiung | 428/311 |
| 4,186,648 A | 2/1980 | Clausen et al. | 428/242 |
| 4,233,359 A | 11/1980 | Mimura et al. | 428/254 |
| 4,331,731 A | 5/1982 | Seike et al. | 428/305.5 |
| 4,501,025 A | 2/1985 | Kuznetz | |
| 4,504,402 A | 3/1985 | Chen et al. | 252/70 |
| 4,525,406 A | 6/1985 | Pollock | 428/137 |
| 4,528,231 A | 7/1985 | Lund | 428/242 |
| 4,572,864 A | 2/1986 | Benson et al. | 428/305.5 |
| 4,581,285 A | 4/1986 | Mahefkey, Jr. | 428/285 |
| 4,581,286 A | 4/1986 | Fottinger et al. | 428/288 |
| 4,588,400 A | 5/1986 | Ring et al. | |
| 4,596,738 A | 6/1986 | Metcalfe et al. | 428/308.4 |
| 4,617,332 A | 10/1986 | Salyer | 524/4 |
| 4,645,697 A | 2/1987 | Torigoe | 428/43 |
| 4,649,895 A | 3/1987 | Yasuki et al. | 126/263 |
| 4,658,515 A | 4/1987 | Oatman | 36/44 |
| 4,708,812 A | 11/1987 | Hatfield | 252/70 |
| 4,711,813 A | 12/1987 | Salyer | 428/402 |
| 4,747,240 A | 5/1988 | Voisinet et al. | 52/173 |
| 4,752,526 A | 6/1988 | Daimon et al. | 428/332 |
| 4,755,407 A | 7/1988 | Mortensen et al. | 428/36 |
| 4,756,958 A | * 7/1988 | Bryant et al. | 428/320.2 |
| 4,797,160 A | 1/1989 | Salyer | 106/96 |
| 4,807,696 A | 2/1989 | Colvin et al. | |
| 4,851,291 A | 7/1989 | Vigo et al. | 428/393 |
| 4,856,294 A | 8/1989 | Scaringe et al. | 62/259.3 |
| 4,869,954 A | 9/1989 | Squitieri | 428/283 |
| 4,871,615 A | 10/1989 | Vigo | 428/398 |
| 4,894,931 A | * 1/1990 | Senee et al. | 36/2.6 |
| 4,908,166 A | 3/1990 | Salyer | 264/22 |
| 4,908,238 A | 3/1990 | Vigo | 427/389 |
| 4,911,232 A | 3/1990 | Colvin et al. | |
| 4,921,743 A | 5/1990 | Hansen et al. | |
| 4,925,732 A | 5/1990 | Driskill et al. | 428/336 |
| 4,936,319 A | 6/1990 | Neubardt | |
| 4,953,544 A | 9/1990 | Hansen et al. | |
| 4,964,402 A | 10/1990 | Grim et al. | 128/80 |
| 4,983,798 A | 1/1991 | Eckler et al. | 219/10.55 |
| 4,989,418 A | 2/1991 | Hewlett | 62/457.4 |
| 5,020,164 A | 6/1991 | Edwards | 2/239 |
| 5,053,446 A | 10/1991 | Salyer | 524/8 |
| 5,106,520 A | * 4/1992 | Salyer | 252/70 |
| 5,141,079 A | 8/1992 | Whitney et al. | |
| 5,143,765 A | 9/1992 | Mair et al. | 428/36.5 |
| 5,148,861 A | 9/1992 | Colvin et al. | |
| 5,176,672 A | * 1/1993 | Bruemmer et al. | 604/385.1 |
| 5,217,782 A | * 6/1993 | Moretz et al. | 428/91 |
| 5,224,356 A | 7/1993 | Colvin et al. | |
| 5,227,230 A | 7/1993 | McGlade | 429/319.1 |
| 5,254,380 A | 10/1993 | Salyer | 428/35.7 |
| 5,290,904 A | 3/1994 | Colvin | 165/10 X |
| 5,366,801 A | 11/1994 | Bryant et al. | |
| 5,378,528 A | 1/1995 | Makoui | 428/219 |
| 5,415,222 A | 5/1995 | Colvin et al. | |
| 5,437,621 A | 8/1995 | Andrews et al. | |
| 5,499,460 A | * 3/1996 | Bryant et al. | 36/43 |
| 5,637,389 A | 6/1997 | Colvin et al. | |
| 5,804,297 A | 9/1998 | Colvin et al. | |
| 5,851,338 A | 12/1998 | Pushaw | |
| 6,004,662 A | * 12/1999 | Buckley | 428/304.4 |
| 6,057,266 A | 5/2000 | Colvin et al. | |
| 6,207,738 B1 | 3/2001 | Zuckerman et al. | |
| 6,298,907 B1 | 10/2001 | Colvin et al. | |
| 6,319,599 B1 | * 11/2001 | Buckley | 428/308.4 |
| 6,373,058 B1 | 4/2002 | McKinney et al. | |
| 6,418,832 B1 | 7/2002 | Colvin | |
| 6,464,672 B1 | 10/2002 | Buckley | |
| 6,503,976 B2 | 1/2003 | Zuckerman et al. | |
| 6,514,362 B1 | 2/2003 | Zuckerman et al. | |

OTHER PUBLICATIONS

"Textiles that Adapt to Heat and Cold", Inside R&D, Oct. 17, 1984, pp. 3–4.

Peg's Promise; The Department of Agriculture studies the use of an inexpensive polymer that could lead to clothing that cools and warms its wearer, by Penny Kron, Apparel Industry Magazine, Sep. 1988.

Fabrics given enhanced thermal properties; Oct. 20, 1986 C&EN p. 15–16.

Majendie, J. L. A.; "Equipment for the Working Diver"; Feb. 1970 Symposium pp. 95 and 108.

Seltzer, Richard; "Fabrics Given Enhanced Thermal Properties"; C&EN; Oct. 20, 1986; pp. 15–16.

Kron, Penny; "PEG's Promise"; Reprint from Apparel Industry Magazine; Sep. 1988.

Bryant, Y.G.; Colvin, D.P.; "Fibers with Enhanced, Reversible Thermal Energy Storage Properties"; Techtextil–Symposium; Jan. 1992.

J.L.A. Majendie p. 95 of "Diver Heating" from Equipment for the working diver; symposium proceedings Feb. 24–25, 1970, Columbus, OH.

Bayes, S. A., "A Nonventing Cooling System for Space Environment Extravehicular Activity, Using Radiation and Regenerable Thermal Storage", SAE Technical Paper Series, $18^{th}$ Intersociety Conf. on Environmental Systems (Jul. 11–13, 1988).

BMDO, "Enhanced Heat Transfer and Storage Materials for Strategic Defense Systems", Triangle Res. & Dev., Small Business Innovative Research, Award date: 1986 (Abstract).

Bue et al., "Advanced Suit Design Analyzer Computer Program", $22^{nd}$ International Conference on Environmental Systems, (Jul. 13–16, 1992).

Case for Mars V, American Astronautical Society, vol. 97, Science and Technology Series, Conf., pp. 509–510 (May 26–29, 1993).

Colvin et al., "Enhanced Heat Transport in Environmental Systems Using Microencapsulated Phase Change Materials", $22^{nd}$ International Conference on Environmental Systems, (Jul. 13–16, 1992).

Colvin et al., "Thermal Management of Electronic Systems Using Diamond Heat Spreaders and Microencapsulated PCM Coolants",1997 National Heat Transfer Conf. (Aug. 1997).

DOD–AF, "Spacecraft Heat Rejection Methods: Active and Passive Heat Transfer for Electronic Systems", Triangle Res. & Dev., Small Business Innovative Research, Award date: 1985–1986 (Abstract).

DOD–AF, "Enhanced Thermal Energy Storage in Clothing With Impregnated PCM", Triangle Res. & Dev., Small Business Innovative Research, Award date: 1987 (Abstract).

DOD–NAVY, "Electrorheological Damper Using MicroPCM Fluid", Triangle Res. & Dev., Small Business Innovative Res., Award date: 1991 (Abstract).

DOD–NAVY, "Enhanced Thermal Energy Storage in Clothing with", Triangle Res. & Dev., Small Business Innovative Res., Award date: 1992 (Abstract).

DOD–NAVY, "Passive PCM Microclimate Body Undergarment Thermal Management System", Triangle Res. & Dev., Small Business Innovative Res., Award date: 1992 (Abstract).

DOD–NAVY, "Using Diamond Film Heat Spreaders and Microencapsulated Phase Change Materials for Electronics Cooling", Triangle Res. & Dev., Small Business Innovative Res., Award date: 1995 (Abstract).

DOD–NAVY, "Lightweight, Regenerative MicroPCM Portable Environmental Control Systems (PECS) Garments", Triangle Res. & Dev., Small Business Innovative Res., Award date: 1996 (Abstract).

DOD–NAVY, "Lightweight, Regenerative MicroPCM Portable Environmental Control Systems (PECS) Garments", Triangle Res. & Dev., Small Business Innovative Res., Award date: 1998 (Abstract).

Kuznetz, L. H., "Space Suit and Life Support Systems for the Exploration of Mars", AIAA Space Proj. & Technol. Conf. 90–3732 (Sep., 1990).

Kuznetz, L. H., "Space Suit and Life Support Systems for the Exploration of Mars", Journal of The British Interplanetary Society, vol. 45, pp. 215–224 (1992).

Mulligan, J. C., et al., "Use of Two–Component Fluids of Microencapsulated Phase–Change Materials for Heat Transfer in Spacecraft Thermal Systems", $6^{th}$ AIAA/ASME Joint Thermophysics and Heat Transfer Conference (Jun. 20–23, 1994).

NASA Tech Brief, "Design Concept/Algorithm for Integrated Passive Body Cooling Garment Using A Phase Change Material (PCM) Slurry", vol. 15, issue 7, p. 44 (Jul. 1991).

NASA. "Space Suit Thermal Control Using Non–Toxic Microencapsulated Two–Phase PCM Fluid", Triangle Res. & Dev., Small Business Innovative Research, Award date: 1988 (Abstract).

NASA, "Spacesuit Glove–Liner with Enhanced Thermal Properties for Improved Comfort", Triangle Res. & Dev., Small Business Innovative Research, Award date: 1989 (Abstract).

NASA Tech Briefs, "Garment Would Provide Variable Cooling", (1991).

NASA Tech Briefs, "Phase–Change Heat–Storage Module", p. 103, (Apr. 1989).

NASA Tech Briefs, "Microencapsulated Phase–Change Materials for Storage of Heat", Machinery, Books and Report, (Jul. 1989).

NSF, "Spinning Performance of Melt–Spun Fibers Containing Microencapsulated Phase Change Material", Triangle Res. & Dev., Small Business Innovative Res., Award date: 2000 (Abstract).

NSF, "Spinning Performance of Melt–Spun Fibers Containing Microencapsulated Phase Change Material", Triangle Res. & Dev., Small Business Innovative Res., Award date: 2001 (Abstract).

NSF, "Two–Component Cutting/Coolant Fluids for High–Speed Machining", Triangle Res. & Dev., Small Business Innovative Research, Award date: 1990 (Abstract).

NSF, "Two–Component Cutting/Coolant Fluids for High–Speed Machining", Triangle Res. & Dev., Small Business Innovative Research, Award date: 1992 (Abstract).

NSF, "Materials for Extending Endurance and Productivity of Underwater Divers in Cold Waters", Triangle Res. & Dev., Small Business Innovative Res., Award date: 1995 (Abstract).

NSF, "Regulation of Moisture and Thermal Microenvironments to Improve Mycoherbicides", Triangle Res. & Dev., Small Business Innovative Res., Award date: 1997 (Abstract) Phase I.

NSF, "Regulation of Moisture and Thermal Microenvironments to Improve Mycoherbicides", Triangle Res. & Dev., Small Business Innovative Res., Award date: 1997 (Abstract) Phase II.

NSF, "Investigation of Phase Change Materials Microcapsules for High Temperature Applications", Triangle Res. & Dev., Small Business Innovative Res., Award date: 1996.

NSF, "Stabilization of Microenvironmental Temperatures on Plant Surfaces with Microencapsulated Phase Change Materials to Prevent Frost/Freeze Damage", Triangle Res. & Dev., Small Business Innovative Res., Award date: 1998.

Quagliaroli, J., et al., "In–House Testing of Thermal Material for Space Application", Amer. Inst. Of Aeronautics & Astronautics (2001) AIAA Paper No. 2001–1450.

SOCOM, "Hybrid Lightweight Protective Body Armor with Impact Absorption and Passive Thermal Management", Triangle Res. & Dev., Small Business Innovative Res., Award date: 1998 (Abstract).

Trevino, L. A., et al., "Advanced Space Suit Insulation Feasibility Study", SAE Technical Paper Series, $30^{th}$ Intl. Conf. on Environmental Systems (Jul. 10–13, 2000).

USDA, "Phyltosphere Microclimate with Micropcms to Improve Mycoherbicides", Triangle Res. & Dev., Small Business Innovative Res., Award date: 1998.

USAF Small Business Innovation Research Program, "Microencapsulated Phase Change Materials for Enhanced Heat Transport and Storage in Electronic Systems", res. Performed by Dr. David P. Colvin.

* cited by examiner

PHASE CHANGE MATERIAL THERMAL CAPACITOR CLOTHING

RELATIONSHIP TO OTHER APPLICATIONS

This patent application is a continuation of patent application Ser. No. 09/033,439 filed Mar. 2, 1998, now U.S. Pat. No. 6,319,599, which is a continuation-in-part of patent application Ser. No. 08/404,419 filed Mar. 15, 1995, now U.S. Pat. No. 5,722,482, which is a continuation-in-part of patent application Ser. No. 07/913,246 filed Jul. 14, 1992 now U.S. Pat. No. 6,004,662, the specifications of which are hereby incorporated by reference in their entirety.

GOVERNMENT RIGHTS

This invention is related to invention disclosures made by the inventor at NASA—Lyndon B. Johnson Space Center, Houston, Tex. The United States government may have certain rights to use this invention.

FIELD OF THE INVENTION

This invention relates to a flexible composite material containing a phase change material for thermal storage and to garments and other articles made from the composite material.

BACKGROUND OF THE INVENTION

The use of phase change materials or PCM's for thermal storage has long been known. In many materials much more heat can be stored as latent heat of phase change than as sensible heat. One of the earliest known applications of this principle is the use of ice as a thermal storage medium for perishable foods. Some of the phase transitions that involve significant amounts of latent heat are solid-to-liquid or liquid-to-gas phase changes or, in certain materials, solid-to-solid phase changes. Another subgroup of PCM's uses reversible exothermic reactions, such as hydration-dehydration or solution-precipitation reactions, for heat storage. The latent heat of phase change can be used for heating or cooling depending on whether the phase change is exothermic or endothermic. In most materials, the phase changes are reversible so that the latent heat storage can be used for either heating or cooling depending on the temperature conditions.

PCM's have recently been applied to personal heating and cooling devices. U.S. Pat. No. 4,856,294 to Scaringe et al. describes a Micro-Climate Control Vest which contains a PCM with a solid-to-liquid phase change between 60 and 90° F. as a cooling medium. The vest may also have an optional second PCM layer of ice and an optional outer insulation layer. Because of the inherent rigidity of the PCM in its solid state, the inner liner which contains the PCM is divided into individual compartments separated by vertical seams that provide folding points in the vest. This provides very limited flexibility in the vest, making it impractical for use during intense physical activity where the rigidity would be a hindrance.

U.S. Pat. No. 4,894,931 to Senee et al. describes a Heating Device for warming body parts, such as the soles of the feet. The device uses a battery powered electric heater and a PCM salt. The PCM salt serves as a heat storage medium and as a temperature regulator for the resistance heater since it can absorb a lot of heat without rising above its melt temperature. This device is described as having a rigid base, which along with the inherent rigidity of the solid PCM salt, would make it unusable for applications where flexibility is important.

U.S. Pat. Nos. 4,572,158 to Fiedler and U.S. Pat. No. 4,077,390 to Stanley et al. both describe heating pads for warming body parts that use a supercooled PCM salt solution for heat storage. The PCM can be dissolved by placing the pad in boiling water. Once the PCM is liquefied, it can be cooled to room temperature without solidifying. A trigger is used to activate the PCM, causing an exothermic crystallization which releases heat at about 135° F. The device is sold with a cloth or neoprene cover to prevent burns when it is placed against the skin. These heating pads are made in small sizes for spot heating parts of the body. Because the solid PCM salt is very rigid, the pad cannot be used for heating large areas of the body where the rigidity would be a hindrance to movement.

U.S. Pat. No. 4,756,958 to Bryant et al. describes a fiber with enhanced thermal storage properties and fabrics made therefrom. The fiber described contains microcapsules of PCM ranging from 1–10 microns in size. While these fibers provide the sought after flexibility, they do not contain enough PCM to have sufficient thermal mass to be of practical use in heating or cooling.

U.S. Pat. No. 4,851,291 to Vigo et al. describes another method of making fibers with thermal storage properties by filling the core of a hollow fiber with a PCM or absorbing a PCM onto the surface of a non-hollow fiber. The PCM's described include cross-linked polyethylene glycol and plastic crystals that have a solid-to-solid crystalline phase change. These fibers can also can be made very flexible, but their geometry does not allow absorption of enough PCM into the containment material to be of practical use in heating or cooling.

SUMMARY OF THE INVENTION

From the preceding discussion it can be seen that the prior art, in all of its attempts, has failed to provide a flexible composite material with thermal storage properties that at the same time provides: 1) sufficient thermal mass for heating or cooling large areas of the body, and 2) enough flexibility to be fashioned into garments or other articles suitable for wear during vigorous physical activity where rigidity would be a hindrance to movement. With this in mind, the objective of the present invention is to provide a highly flexible composite material that contains a high thermal mass of a phase change thermal storage material. The phase change thermal storage material is dispersed within the composite material such that the entire composite is flexible when the phase change material is in a high energy or low energy state. In various embodiments, the composite material can be made to heat or cool the body or to act as a thermal buffer to protect the wearer from changing environmental conditions. To help with this objective, the material may also include an external thermal insulation layer and/or an internal thermal control layer to regulate the rate of heat exchange between the composite and the skin of the wearer. Another important objective is to provide a flexible thermal storage composite material that can easily be fashioned into garments or other articles, such as blankets, that can be worn for their thermal properties.

Other secondary objectives of the invention are to provide a flexible thermal storage composite material that also provides 1) a path for evaporation or direct absorption of perspiration from the skin of the wearer for improved comfort and thermal control, 2) heat conductive pathways within the material for thermal equalization, 3) surface treatments for improved absorption or rejection of heat by the material, and 4) means for quickly regenerating the thermal storage capacity for reuse of the material.

In keeping with these objectives, the simplest embodiment of the present invention provides a composite material that has a phase change material incorporated into a flexible matrix material. In a second embodiment, the composite also includes an external thermal insulation layer and an internal thermal control layer to modify the surface temperature experienced by the skin of the wearer. Other embodiments feature moisture wicking components or other components that add different thermal properties to the composite. In each embodiment, the PCM may be chosen to provide heating, cooling or environmental buffering.

Exemplary applications of the composite materials are also described which take advantage of the composite's thermal characteristics. The examples described include a diver's wet suit, ski boot liners, thermal socks, gloves and a face mask for cold weather activities, and a metabolic heating or cooling blanket useful for treating hypothermia or fever patients in a medical setting.

DESCRIPTION OF THE PREFERRED EMBODIMENTS

Figure 1:
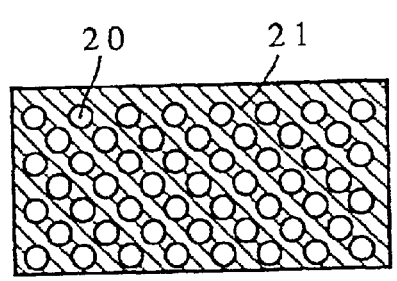
FIG. 1 shows a cross section of a flexible PCM composite.

FIG. 1 shows a flexible composite material with a PCM 20 distributed within a flexible matrix material 21. The flexible matrix material 21 is preferably a flexible polymer or a polymer foam, either open cell or closed cell. The PCM 20 can be one of several possible materials capable of absorbing or releasing heat as the latent heat of phase change. The thermal characteristics of the composite can be tailored by the choice of the PCM and the matrix material, as well as the ratio of the concentration between the two materials chosen. The actual choice of the PCM depends on the intended application of the composite material and on the desired characteristics. The criteria for choosing a PCM are discussed more fully in a separate section below.

If a solid-solid phase transition PCM is chosen, the PCM may be added directly to the matrix material in the form of pellets or particles as it is being formed. If a solid-liquid phase transition PCM is chosen, the PCM should be encapsulated. The PCM can be in microcapsules or in larger capsules or a mixture of sizes. There are two reasons why it is preferable to encapsulate the PCM in the composite: first, to prevent it from migrating when it is in the liquid state and, second, so that the PCM does not form one solid inflexible mass as it cools. If a solid polymer matrix is used, then the matrix material can also serve as the encapsulant. If an open or closed cell polymer foam is used as the matrix, the PCM should be encapsulated within a polymer or other nonporous material before being added to the foam. Another method of preventing the liquid PCM from migrating within the composite is to absorb it into a material that holds the PCM captive, such as particles or fibers of polyacrylic or carboxymethyl-cellulose, before adding them to the matrix. Other methods of preventing PCM from migrating are to mix the PCM with a third substance to create a paste or other form to ease incorporation into a matrix Examples of the structure in FIG. 1 have been successfully made using a mixture of coconut oil and rice oil as the PCM and latex as the encapsulant and matrix material.

Figure 2:
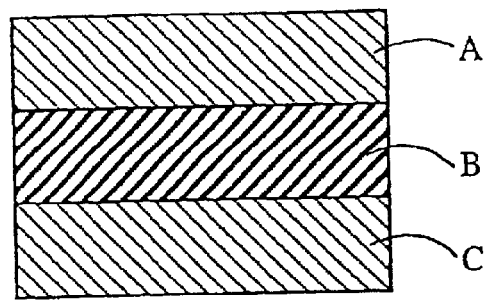
FIG. 2 shows a cross section of a multilayer flexible PCM composite having an insulating outer layer and a thermal control inner layer.

FIG. 2 shows a multilayer flexible composite material containing a PCM layer. The composite may be made by laminating diverse materials together or it may be made of a single matrix material with the PCM concentrated within one layer of the composite.

Layer A, on the exterior surface of the composite, is a thermal insulation layer to reduce the heat exchange between the PCM and the environment and to protect the wearer from harsh exterior temperatures. The ideal material for this layer in most applications is a flexible polymer foam.

Layer B is the layer which contains the PCM. It may be a matrix material with the PCM distributed within it, as in FIG. 1, or other structures may be used to hold the PCM in place.

Layer C, on the interior surface of the composite, is a thermal control layer, whose function is to regulate the rate of heat exchange between the PCM and the skin of the wearer and thereby keep the skin contact surface at a comfortable temperature. If the PCM transition temperature is within the comfort range for skin contact, then layer C might be a simple barrier layer to contain the PCM. If the PCM transition temperature is outside the comfort range, either too hot or too cold, then layer C should be a thermally insulating material, such as plastic foam to reduce heat exchange. In most applications, it is preferable to have layer C thinner than layer A so that the PCM will have better thermal coupling with the wearer's skin than with the external environment. The thermal control layer can also be used to increase the rate of heat exchange. For this purpose, layer C can be made to include fibers or films of thermally conductive material to provide a thermally conductive pathway between the PCM and the skin of the wearer.

Figure 3:
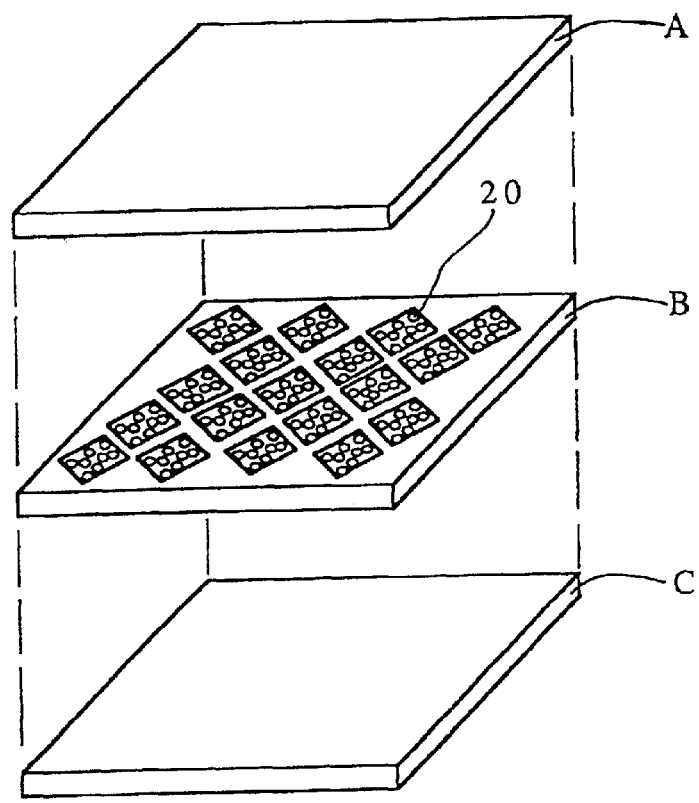
FIG. 3 shows a laminated construction for a multilayer PCM composite.

FIG. 3 shows one embodiment of the multilayer flexible composite constructed by laminating layers of different materials together. Layer A is a layer of closed cell neoprene foam that acts as thermal insulation. Layer B includes an inner web of perforated neoprene foam. The webbing serves as the matrix which contains the PCM and lends structure to the composite. The PCM 20 is preferably in peletized form so that the rigidity of the PCM in its solid form does not adversely affect the flexibility of the composite. Layer C is a thin layer of closed cell neoprene foam. Layers A, B, and C are bonded together to make the composite material.

Figure 4:
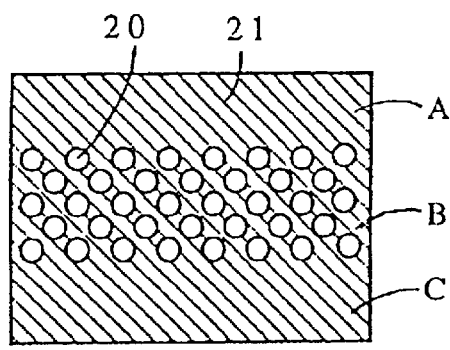
FIG. 4 shows a monolithic construction for a multilayer PCM composite.

FIG. 4 shows an embodiment of the multilayer flexible composite that is made as a monolithic structure without laminations. The matrix material is preferably a flexible polymer or a polymer foam.

One method of manufacturing the composite is by casting it in large sheets or as preshaped parts. Any castable material can be used as the matrix in this method. Satisfactory materials used for prototypes of this embodiment include latex, silicone, polyurethane, polyurethane foam, and other natural and synthetic rubbers.

Other materials suitable for use as matrices are: ABS, SAN, acetal, acrylic, alkyd, allyl, amino, cellulosic, epoxy, fluoroplastics, liquid-crystal polymers, nylon, phenolic, polyamide, polyimide, polycarbonate, polyester, polyetheretherketone, polyetherimide, polyolefins, polypheylene ether, polypheylene sulfide, polystyrene, polyurethane, polyvinyl chloride, sulfone polymers, laminated plastics, structural foam, nitrile rubber, butyl rubber, viton, mylar, thermoplastic elastomers, thermoplastic rubbers, ethylene vinal acetate, polyureas, kevlar, aramide, aromatic polyamides, fluorinated hydrocarbons, and parylene.

The suggested process for producing the monolithic composite is as follows: Layer A of the matrix material 21 is cast to the desired thickness in a mold or on a very flat surface. Layer A is allowed to partially, but not fully, vulcanize. Layer B of the matrix material containing a high concentration of granulated or encapsulated PCM 20 is cast over layer A and smoothed to the desired thickness. Layer B is also allowed to partially vulcanize. Layer C of the matrix material is cast over layer B and smoothed to the desired thickness. The entire composite is then allowed to fully vulcanize. Because successive layers of the matrix material are added before the previous layers are fully vulcanized, bonding between the layers is as strong as the matrix material itself. There are no weak points that could cause delamination of the composite.

Optionally, outer or inner linings of fabric or other materials may be added to the composite at the beginning or the end of the process. In some embodiments, this fabric layer may constitute the entirety of the outer or inner layer.

The described process is given by way of example only. Those skilled in the art of polymer fabrication will, no doubt, be able to devise other processes or variations on the described process to arrive at the same result. For instance, a thermal storage composite could also be made by one of the following processes:

1. Dispersing an absorbent, super absorbent, etc, into an open cell matrix then adding the PCM to the matrix. As the absorbent now swells, it will tend to lock the absorbed PCM into the open cell matrix.
2. Injecting the PCM into a cavity or gel material. For example, new synthetic skins have been developed that permit injection of antibiotics or other substances.
3. Creating a flexible embodiment containing the phase change material via vulcanization to form factice from unsaturated vegetable oils such as tung oil and linseed oil ("Chemical Reactions During Vulcanization," E. A. Hauser and M. C. SZE). The oils forming the factice then become the phase change material.
4. Supersaturation of a PCM salt solution, absorption of this solution into an open cell matrix or foam then subsequent evaporation of the solvent.
5. Incorporation of micro encapsulated, macro encapsulated, etc. PCM into a froth such as the polyurethane froths used to created foam backings on carpet (ICI Polyurethane's Handbook, D. Sparrow).
6. Use of macro encapsulation and pharmaceutical hard, soft, gel, etc. drug encapsulating techniques to contain the PCM prior to incorporation into the matrix (Micro capsule Processes and Technology, A. Kondo).
4. Absorption, adsorption, etc. of the PCM onto a membrane bound with the absorbing, adsorbing, etc. material.
5. Absorption of natural fats and oils into unvulcanized natural rubber, rubber, silicones, etc. or other natural and synthetic polymers that absorb the PCM of interest.
6. The use of molding, vacuum forming and thermoforming techniques for macro encapsulation of a continuum of PCM particles during the formation of a laminate.
7. Deposition of micro encapsulated PCM onto thin films. An example of this form of carrying micro capsules is given in Polymers for Engineering Applications by R. Seymour.
8. Forming aggregates with granules or encapsulated PCM's by dispersing the particles into a gel, or other flexible bonding material to form an aggregate.
9. Forming jellies of PCM's using pectin, gelatin (proteins), then dispersing these jellies within sealed matrices.
10. Creating a rubber, rubber gels or other gels as described by S. S. Kistler in "Coherent Expanded Aerogels," however, a PCM is used in the solvent step.
11. Selective absorption of embodiment of the PCM into cellular (natural and synthetic) membranes or matrices. Techniques might include dialysis and the use of absorbents, adsorbents, etc. within the membrane for containment of the PCM upon its entry into the cellular space. Techniques may also include Graham's method of cell fixation whereby liquids in gelatinous tissues are sequentially replaced with other liquids, miscible in the first, such that the final replacement liquid is a paraffin. In this intended application, the process is designed so that the final liquid is chosen to be the PCM itself. (Graham, "On the properties of Silicic Acid and other Analogous Colloidal Substances," The journal of the Chemical Society, 1864). Graham's same process forms the foundation for the formation of alcogels, aerogels, etc. as described in S. S. Kistler's "Coherent Expanded Aerogels and Jellies," Nature, 1931 wherein the aerogel process is stopped at the stage that contains the desired cm formation.
12. Incorporating the step of macro encapsulating the PCM into a higher melting point, semi-stable form such as a paraffin prior to incorporation into a matrix.
13. Spraying a sheet of coating over a dispersion of PCM to bond the PCM to another layer in the composite.
14. Mixing the PCM with a third substance to create a paste in order to stabilize it while in a liquid state during lamination.

Figure 5:
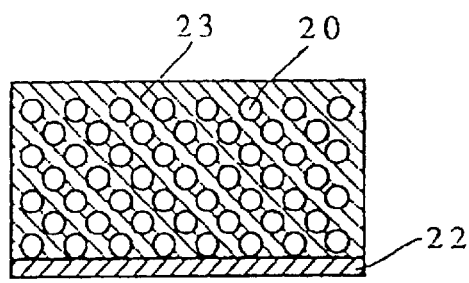
FIG. 5 shows a PCM composite with a semipermeable membrane for moisture control.

For some applications of the PCM composite it will be desirable to incorporate a moisture transport mechanism into the composite to transport perspiration, condensation, or other moisture away from the skin of the wearer. FIG. 5 shows a PCM composite with one possible moisture transport mechanism. The composite is made with an open cell foam or other porous material as the matrix material 23 so that it is permeable to moisture. The PCM is distributed within the matrix as pellets or capsules. The skin surface of the composite is lined with a semipermeable membrane 22 which is permeable to water vapor, but impermeable to liquid water. One possible material for this semipermeable membrane is expanded polytetrafluoroethylene which is available under the trade name Gore-Tex® from W. L. Gore and Co. Another semipermeable membrane material usable in this application is cellulose acetate. The membrane allows water vapor from perspiration to diffuse through the composite while preventing liquid water from entering the open cell matrix. If desired, another layer of semipermeable membrane may also be laminated to the exterior surface of the composite. One embodiment of this has been made using particles or capsules of PCM bonded between two Gore-Tex® membranes using an adhesive to form a porous matrix.

Figure 6:
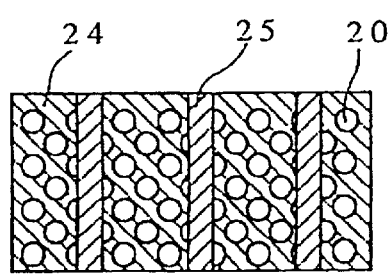
FIG. 6 shows a PCM composite with wicking elements for moisture transport.

FIG. 6 shows another possible embodiment of the composite incorporating a moisture transport mechanism. In this example, the matrix material 24 is a closed cell foam or a solid polymer which is impermeable to moisture. To allow moisture to be transported through the impermeable matrix material, moisture transport elements 25 are added that bridge the composite from the inner surface to the outer surface.

In their simplest form, the moisture transport elements may be nothing more than vents that allow perspiration and water vapor to escape. In their preferred form, they are wicking elements 25 that are made of a moisture absorbent material that conducts moisture from the skin surface to the exterior of the composite. Superabsorbent materials, such as carboxy-methyl-cellulose fibers, may also be used as the wicking element. It is also possible to incorporate dessicants into the composite to absorb moisture.

Figure 7:
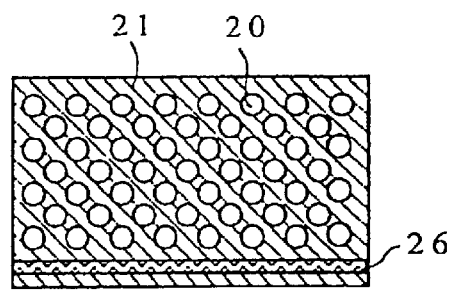
FIG. 7 shows a PCM composite with a thermal conduction layer.

Another feature that may be added to PCM composite is a thermally conductive material that helps to distribute the heat within the composite. FIG. 7 shows a PCM composite that contains a heat equalization layer 26 of thermally conductive material. The layer 26 may be made from a conductive film or a network or mesh of fine wires or heat conductive fibers or a mat of random wires or fibers. The heat equalization layer 26 distributes heat horizontally within the composite material so that hot spots are eliminated and there is an even temperature distribution all over the skin surface.

Figure 8:
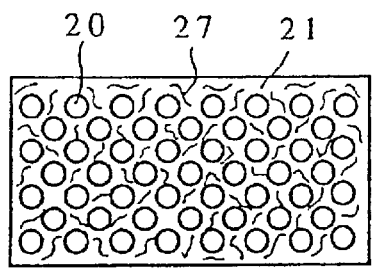
FIG. 8 shows a PCM composite containing thermally conductive fibers.

FIG. 8 shows a PCM composite that contains heat conductive fibers or wires 27 distributed throughout the matrix material 21 to distribute heat horizontally and vertically within the composite. The advantage of this is that it makes more effective utilization of the PCM. The improved thermal coupling between the skin surface and the PCM shortens the thermal path for absorption or release of heat from the PCM.

Another effective way to use thermally conductive materials in the PCM composite is to use them for encapsulating the PCM. Thin metal capsules or capsules of another thermally conductive material surrounding the PCM would greatly improve the thermal coupling with the PCM.

Another method of affecting the thermal coupling between the PCM composite and the skin is to change the contact pressure between the two surfaces. Increasing the contact pressure will increase the rate of heat transfer and decreasing the pressure will lower the rate of heat transfer. One way to accomplish this is by adding an inflatable bladder within the composite material or within a garment containing the composite so that fluid pressure can be used to regulate the contact pressure and therefore the thermal coupling. Another way would be to add elastic straps or hook-and-loop fasteners to increase contact pressure between the PCM composite and the skin.

Figure 9:
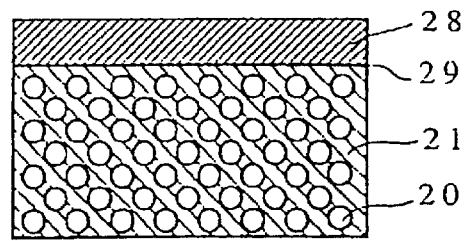
FIG. 9 shows a PCM composite with an aerogel insulation layer and a solar absorption surface.

Another feature to enhance the thermal properties of the PCM composite is the addition of a solar absorption surface to the exterior of the composite material. By absorbing solar radiation and converting it to heat, the solar absorption surface acts to regenerate the PCM in a warming garment. In its simplest form this could be the addition of a dark colorant or a dark material to the exterior surface of the composite. In another embodiment, shown in FIG. 9, a transparent aerogel 28 has been added to the outer surface of the composite to act as a very effective insulation layer and as a window to solar radiation. The solar absorption surface 29 is placed at the interface between the aerogel layer and the PCM-containing layer.

Figure 10:
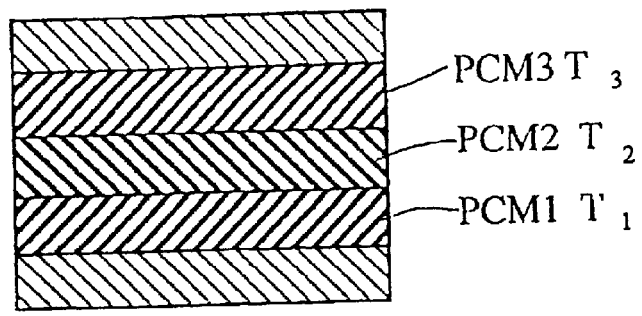
FIG. 10 shows a multilayer PCM composite using three PCM's with different transition temperatures.

In some applications it may be advantageous to combine two or more PCM's having different transition temperatures into the composite material. FIG. 10 shows a schematic diagram of a multilayer PCM composite with three PCM layers having different transition temperatures.

This arrangement can be used to overcome one of the drawbacks inherent in some of the prior art PCM applications. Namely, some PCM garments start to lose some of their effectiveness after the PCM near the skin has undergone its phase transition. This is because the thermal path length is longer to the unchanged PCM that is farther from the skin. One solution to this is to add conductive materials to the composite as previously described. The other solution is to use multiple PCM's with different transition temperatures. To understand how this works, please refer to FIG. 10.

For the sake of discussion let us say that the PCM composite of FIG. 10 is to be used for a cooling garment. PCM's 1, 2, and 3 should be chosen so that they have progressively lower transitions temperatures moving away from the skin surface, that is, $T_1 > T_2 > T_3$.

If the transition temperatures and the thicknesses of the layers 1, 2, and 3 are properly chosen, then each layer will be equally effective in cooling the skin of the wearer because the longer thermal path length to the more distant layers will be compensated by the lower transition temperature of the PCM. Thus, the rate of heat absorption of the composite will remain relatively constant until all of the PCM has undergone its phase transition.

Mathematically, the heat flux, Q, is proportional to the temperature difference, $DT = T_{skin} - T_{transition}$, divided by the thermal resistance, R, which is determined by the thermal path length:

$$Q \alpha \Delta T / R = (T_{skin} - Ti) / Ri$$

where $T_1 > T_2 > T_3$ and $R_1 < R_2 < R_3$

Figure 11:
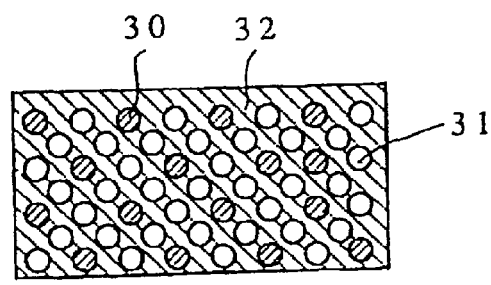
FIG. 11 shows a PCM composite using two PCM's with different transition temperatures randomly distributed throughout the composite.

By the proper choice of $T_1$, $T_2$, and $T_3$, $Q_1$, $Q_2$, and $Q_3$ can be made approximately equal so the rate of heat absorption of the composite will remain relatively constant until all three layers of PCM are exhausted Another way to incorporate multiple PCM's into a single composite is to evenly distribute two or more encapsulated PCM's 30, 31 throughout the matrix 32 as shown in FIG. 11. This arrangement can be used when thermal protection is needed at two or more different temperatures. One PCM can be a heating PCM 30 and the other can be a cooling PCM 31 to incorporate both functions into a single composite.

Phase Change Materials

As mentioned in the background discussion, a phase change material or PCM is any material capable of storing thermal energy as latent heat of a phase change. There are a great many materials that exhibit this property. Table 1 shows some of the materials useful as PCM's. The choice of which PCM to use for thermal storage in the flexible PCM composite of this invention depends principally on two factors: the latent heat of the phase change and the transition temperature. A number of secondary factors may also affect the choice of PCM's, such as density, low toxicity and low flammability. In general, the higher its latent heat of phase change is, the better a material will be as a PCM because more thermal energy can be stored in it. The choice of transition temperature depends largely on the intended function of the composite. The PCM's can be categorized as heating PCM's, cooling PCM's and buffering PCM's. Heating PCM's are materials whose phase transition temperature is above the body's normal skin temperature. When a heating PCM is warmed above its transition temperature and placed in thermal contact with the skin, the temperature gradient will be such that heat flows from the PCM into the body. More extreme heating PCM's will also have their transition temperatures above the body's core temperature.

Cooling PCM's are defined as those materials whose phase transition temperatures are below the body's normal skin temperature. When a cooling PCM is chilled below its transition temperature and placed in thermal contact with the skin, the temperature gradient will make heat flow from the body into the PCM.

A buffering PCM is a material whose phase transition temperature is slightly below normal skin temperature so that it can serve to absorb or release heat depending on environmental and metabolic conditions. Thus, a buffering PCM could also be classified as a mildly-cooling PCM. A buffering PCM can be effectively used to help a body maintain thermal equilibrium by regulating heat flow from the body. A buffering PCM can also be used to protect a body from rapidly changing or cycling environmental temperatures.

This buffering function is most effective when the PCM is at its phase transition temperature and some of the PCM is in its high energy state and some is in its low energy state. Let us say for instance, that a garment is made of a flexible PCM composite using a solid-liquid PCM with a transition temperature of 60° F. The initial condition of the PCM is at 60° F. and some of the PCM is solid and some is liquid when the garment is donned. The temperature of the PCM is lower than the wearer's skin temperature so there is a temperature gradient that causes heat to flow from the body into the PCM. Instead of heating up the way an insulating garment would, the solid PCM serves as a constant temperature heat sink absorbing heat as it changes to a liquid, not heating up as long as there is solid PCM in the composite.

Now, let us say that the wearer begins a job or a recreational activity that involves entering a cold environment. The outside temperature drops and the PCM begins to give up heat to the surrounding environment. However, because of the stored heat in the liquid PCM which is given up when the PCM turns to a solid, the PCM maintains a constant 60° F. as long as some liquid PCM remains. Although the outside environment may drop to arctic temperatures, the skin experiences a constant temperature of 60° F. which keeps the wearer comfortable.

Next, if the wearer moves into a hot environment with a temperature above body temperature, the temperature gradient is reversed and the PCM begins to absorb heat from the environment. Again, instead of heating up, the garment keeps a constant temperature of 60° F. as long as there is solid PCM within the composite to absorb heat. If the wearer had been wearing an insulating garment, he or she would have had to remove the garment to avoid overheating and the dangers of hyperthermia. Thus, a garment made with a buffering PCM within the flexible PCM composite will maintain a comfortable, constant temperature environment for the body despite drastic changes in the external environment.

A buffering PCM can also be used to accommodate large changes in metabolic rate in constant or changing environmental conditions. To illustrate this principle, let us consider the example of two crosscountry skiers engaged in a biathlon race. Skier 1 is wearing an ordinary insulating garment and skier 2 is wearing a garment made with flexible PCM composite. At the beginning of the race both skiers are warm and comfortable, appropriately dressed for the outdoor conditions. When they start skiing, however, skier 1 starts to heat up because his insulating garment prevents him from rejecting the excess metabolic heat to the environment. Skier 1 must either stop and remove some of his insulation or he must endure the overheating, which will cause excessive perspiration and perhaps hyperthermia. Skier 2, on the other hand, maintains his thermal comfort because his PCM garment absorbs the excess metabolic heat without any rise in temperature.

After skiing the first leg of the race, both biathletes must stop to shoot at a rifle target. When their activity level drops so does their metabolism. Skier 1, depending on his insulating garment for warmth, starts to chill, especially if his garment is sweat soaked, thereby losing its insulating value. This chilling can greatly affect the racer's marksmanship. Skier 2, however, stays warm as his PCM garment stops absorbing heat and starts releasing heat to maintain a constant comfortable temperature. This thermal cycling continues for the rest of the race, with skier 1 getting the worst of it each time. At the end of the race, skier 1 must quickly don a heavy parka or go indoors to avoid a severe chill, while skier 2 can remain warm and comfortable for some time because of the heat stored up in his PCM garment. Thus a buffering PCM composite can be used to maintain a constant thermal environment for the wearer in spite of temperature changes in the external environment or changes in the wearer's metabolic rate.

PCM's in Absorbent Materials

As briefly mentioned in the detailed description above, absorbent materials can be used as an alternative to encapsulation to hold the PCM and to keep it from migrating within the composite. Absorbent materials such as open cell polymer foam or cellulose fibers can be used to absorb a PCM while it is in the liquid state. Superabsorbent materials such as crosslinked polyethylene oxide, polyacrylates or carboxy-methyl-cellulose in the form of particles, fibers or films can also be used to absorb certain PCM's. The superabsorbents have the advantages that they absorb a higher percentage of their own weight in PCM and that the PCM is held tenaciously within the superaborbent so that it will not migrate even in the liquid state.

Some solid-liquid PCM's can be easily absorbed into an absorbent or superabsorbent material when they are in the liquid state. PCM salts can be introduced into an absorbent in solution or as a supersaturated solution, then the solvent can be evaporated to leave the PCM salt behind. Some PCM's will not readily absorb into certain absorbent or superabsorbent materials even when they are in the liquid state. This problem can sometimes be overcome by introducing the PCM into the absorbent using a method based on Graham's method of cell fixation. In this method, a compatible liquid such as water is first absorbed into the material; the water is then gradually replaced with another liquid like an alcohol that is miscible with the water. Once the alcohol has completely replaced the water, then stronger and stronger solutions of an alcohol soluable PCM, like a parafin wax or an oil, can be used to replace the alcohol with a high concentration of the PCM. In this way, a PCM can be gradually introduced into a superabsorbent material that normally is only absorbent for water. This is only one simple example of this process, other types of PCM materials can be introduced to absorbent materials with variations on this process using suitable solvents.

PCM composites of the types shown in FIGS. 1 and 4 can be made by absorbing a PCM into small particles of foam or a superabsorbent material and adding them to the matrix material in place of the pellets or capsules of PCM previously described. Likewise, the laminated composite structure of FIG. 3 can be made by replacing the PCM capsules shown with PCM contained in particles of absorbent materials or small blocks of absorbent cut to fit the perforations in layer B. In the multilayer composite structure shown in FIG. 2, the entire layer B can be replaced with a layer of absorbent foam or a layer of superabsorbent material.

To avoid having the absorbent layer become inflexible when the PCM solidifies, a combination of different melting point waxes can be used as the PCM. When a combination like this is used the lower melting point wax will keep the mixture flexible until all of the waxes are below their freezing points. Alternately, the layer of PCM-containing absorbent material can be broken up with a flexible network or webbing that provides flexibility to the layer when the PCM is solidified.

Some absorbent and superabsorbent materials swell significantly when they absorb another material. A superabsorbent is generally defined as a material which absorbs more than 20 times its weight of the substance to be absorbed. This property can be used to advantage when making the flexible PCM composite. Particles of the absorbent material by itself can placed into the internal spaces of an open cell foam or a fibrous network and then swelled in place by allowing them to absorb the PCM. The absorbent particles with the PCM become locked into place inside the matrix when they swell up. The result is a flexible composite material containing the PCM within a foam or fibrous matrix.

Suitable absorbents and super absorbents include cellulose, cotton, open-called foam, silica, polypropylene, carboxymethyl groups, diethylaminoethyl groups, styrene devinylbenzene copolymers with selected functional groups, polyacrylamides and their copolymers, agarose gels, polystyrene, hydroxyapatite, alumina, silicone, celotex (sugar cane fiber), methyl cellulose, carboxymethyl cellulose, poly-N-vinyl-2-pyrrodine and its copolymers, hydrogels, dextran, starch grafted polyacrylate polymers, down, synthetic downs and ethylene oxides. In addition, several absorbant products are available on the market for oil spill recovery. These include Envirobon 403 from Petroleum Environmental Technologies, Nochars A610/A650 bonding agent from Nochar Inc., Elastol (polu-iso-butylene) and Elastasorb from Beneral Technology, rubberizers and Magic Sorb from Devcon. Obviously that absobent must be matched to the substance to be absorbed.

Another embodiment of the invention involves phase change materials that change phase from a liquid to a gaseous state to absorb thermal energy. One example involves absorbing a liquid, such as ethanol or isopropanol, into a superabsorbant material such as ethylene oxide. The ethylene oxide can be crosslinked to make it structurally stable and/or reinforced with a webbing material. This creates a composite material which has a high percentage of the phase change liquid in the matrix. Such a composite can be used for cooling febrile patients by evaporative cooling as the phase change liquid in the matrix changes from a liquid to a gaseous state to absorb thermal energy. The composite can also be made with a perforated barrier material around the outside to regulate the evaporation rate of the phase change liquid. Alternatively, the composite can be made with an imperveous barrier material on one side to prevent the liquid from contacting the patient's skin. The phase change liquid in the matrix can be recharged by soaking the material in the liquid. This has an important advantage over the traditional method of using alcohol baths for cooling febrile patients in that the cooling effect can be sustained for an extended period of time because of the high percentage of phase change liquid that can be absorbed into the superabsorbant.

Regenerating the Flexible PCM Composite

Once all of the PCM in the composite material has been exhausted, that is, all of the PCM has undergone its phase transition, the PCM must be regenerated to its original state before the material can be used again. The simplest way to regenerate the PCM is to place the material in an environment with the correct temperature. A cooling garment may be placed in a refrigerator or freezer or any other cold place to resolidify the melted PCM. A heating garment may be placed in an oven, a steam cabinet, or boiling water to melt the solidified PCM.

For a thermal buffering garment, with a moderate transition temperature, the PCM may be regenerated without special equipment. For instance, if a buffering PCM has a transition temperature below normal room temperature, the material can be reheated by simply taking it indoors or into a heated car and allowing the temperature to equilibrate.

Of course, the matrix material and any encapsulant or adhesive used to make the composite must be chosen to withstand the temperature extremes of the regeneration cycle.

Figure 12:
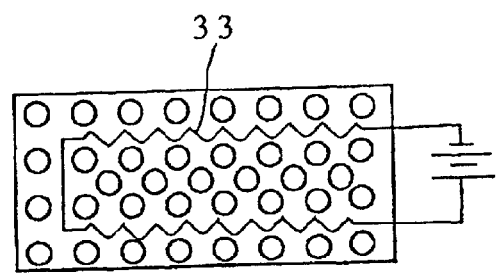
FIG. 12 shows a PCM composite having an electrical resistance heater for regenerating the PCM thermal storage.

To make the regeneration step faster or more convenient, features may be added to the composite to heat or cool the PCM. FIG. 12 schematically depicts a flexible PCM composite with an electrical resistance heater 33 to regenerate the PCM in a heating garment. Another way to use electrical energy to regenerate the PCM is with a thermoelectric (Peltier effect) heat pump. This approach has the advantage that it can be used to heat or cool the material, depending on the current flow in the device.

Rather than including these regeneration devices in the PCM composite, it is also possible to make an auxiliary device that serves to regenerate the PCM. For instance, a flexible bag for storing a PCM garment between uses can incorporate an electrical device for heating or cooling the garment inside. A carrying case or a storage cabinet could also be equipped with regenerating devices such as these.

Chemical means may also be employed to regenerate the PCM or to supplement its effectiveness. An exothermic chemical reaction can be used to heat the PCM composite to regenerate it. Likewise an endothermic chemical reaction can be used to cool the composite. If such an exothermic or endothermic reaction is thermally coupled to the PCM composite while the user is still wearing it, it can be used to supplement the effectiveness of the PCM in heating or cooling or to extend the operation time of the composite.

Another way to regenerate the PCM in the composite is to place it in thermal contact with another PCM. For instance, a cooling garment can be placed into ice to solidify its melted PCM. The reason for doing this instead of using ice as the primary PCM is that the temperature of ice is too low for comfort in long-term contact with the skin. The PCM in the composite can be chosen so that the transition temperature is within the body's comfort range.

If a secondary PCM is placed in thermal contact with the composite while the user is wearing it, the primary PCM can be regenerated while it is still in use. Replaceable layers with the secondary PCM can be used to extend the operation time of the composite.

Other ways of facilitating the regeneration of the PCM composite include making it susceptible to efficient forms of heating such as microwave or induction heating. Some PCM's, such as polyethylene glycol, are naturally susceptible to microwave heating. Other PCM's, for instance most of the PCM salts, cannot be heated with microwaves. For these materials, a susceptor can be added to the PCM or the matrix or the encapsulation material to absorb the microwaves and convert their energy to heat which regenerates the PCM.

Likewise, if induction heating is desired, a susceptor material such as stainless steel can be added to the composite in the PCM, the matrix, or the encapsulant to absorb electromagnetic waves and convert their energy to heat. One way to control the induction heating and prevent overheating the composite and damaging it, is to choose a susceptor material whose Curie temperature is above the transition temperature of the PCM, but below the safe maximum temperature limit of the composite. When the susceptor reaches its Curie temperature it will lose its susceptibility to induction heating until the temperature falls below the Curie point. Thus, the temperature will oscillate around the Curie temperature to quickly and safely heat the composite and regenerate the PCM.

The flexible PCM composite of this invention was designed to provide passive heating and cooling for garments and other articles. It is also possible to combine the PCM composite with active heating or cooling systems to enhance the effectiveness of both. For instance, a PCM composite inner liner can be worn under a space suit that has an active environmental control system. Or a heat exchanger can be coupled to the PCM composite for additional heating or cooling or to regenerate the PCM in use.

The PCM composite would be beneficial to the heating or cooling system. The heat capacity of the PCM composite can be used to reduce peak loads on heating/cooling systems and to maintain the temperature during temporary power outages or disconnections. The temperature stability of the PCM material would also allow the temperature controls of the heating/cooling system to be made less sophisticated because the PCM will protect against overheating or overcooling.

In order to accommodate connection of the PCM composite to an active heating or cooling source, the composite can be made with tubes or passages for a fluid or other heat exchange medium.

THERMAL CONTROL EXAMPLES

Example 1

Thermal Capacitor Diving Suit

The following example of a phase change material thermal capacitor diving suit has been chosen to illustrate the benefits of the present invention. The use of a phase change material thermal capacitor diving suit offers a unique approach to both buffer the individual from extreme environments and simultaneously provide the cooling required to absorb heat generated in the body at a rate that maintains thermal comfort and/or prevents hypothermia or hyperthermia. The same thermal design method is applicable to the other embodiments of the invention described elsewhere in the specification.

Figure 16:
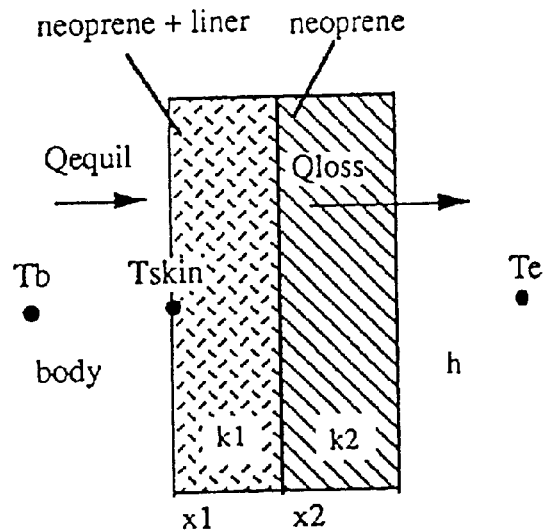
FIG. 16 shows a cross section of prior art traditional wet or dry suit.

A simplification of the steady-state heat transfer process in a prior art diving suit is shown in FIG. 16. Many analytical and experimental algorithms exist, along with computer programs thereof, for determining the allowable rate or quantity of net heat loss from or input to the body to maintain thermal comfort and protection from hypothermia and hyperthermia. The former allowable heat loss or gain is referred to, herein, as $Q_{comfort}$. For a given environment and expected metabolic rates, one can determine the component, $Q_{equil}$, that summed with the respiratory heat losses, sensible and latent heat losses through the skin for areas not covered by the suit, heat loss from water leakage into the suit, etc. maintains $Q_{comf}$ within the heat storage bandwidth chosen. It is realized that convective cooling from water leaking into the suit is an important mode of heat exchange and it is important to minimize this mode of heat exchange by sealing the suit as well as possible. The example below is an ideal case to demonstrate the difference between heat loss across the diving suit with and without a phase change layer. For example purposes only, suppose that the following conditions are true:

$T_{skin}$=90 F
$T_{e1}$=43 F
$T_{e2}$=33 F
$x_1$=3/16"
$x_2$=3/16"
$k_1$=0.03 B/hr-ft-F
$k_2$=0.02 B/hr-ft-F
h=150 B/hr-ft$^2$-F
$A_f$=18 ft$^2$
$C_{pf}$=0.83 B/lbm-F
$Q_{equil}$=625 B/hr From these givens, one can compute $Q_{loss}$ according to equation [1], below, to be equal to 646 B/hr in a 43 F environment and 784 B/hr in a 33 F environment. From the difference between $Q_{loss}$ and $Q_{equil}$, one can conservatively estimate a drop in body temperature equal to 0.2 F/hr for the first case and 1.3 F/hr for the latter. Although this is less likely the case, had $Q_{equil}$ exceeded $Q_{loss}$, a rise in body temperature would occur with a tendency towards overheating.

$$Q_{loss} = \left[ \frac{1}{\frac{x_1}{k_1 A} + \frac{x_2}{k_2 A} + \frac{1}{hA}} \right] (T_{skin} - T_e) \quad [1]$$

The disadvantage of the current practice to strictly use insulation for thermal control is that the thermal resistance is fixed in the diving suit. As explained above, to avoid overheating or chilling, i.e. thermal discomfort, a balance must be achieved between the heat desired to be removed from the body to maintain comfort, $Q_{equil}$ and the actual heat flow out of the suit, $Q_{loss}$. Since environmental conditions change constantly and since thermal conditions of the body are directly linked to the changing environment through this fixed heat transfer path, no latitude exists to achieve this balance at conditions other than those at the single environment for which a solution exists.

Figure 17:
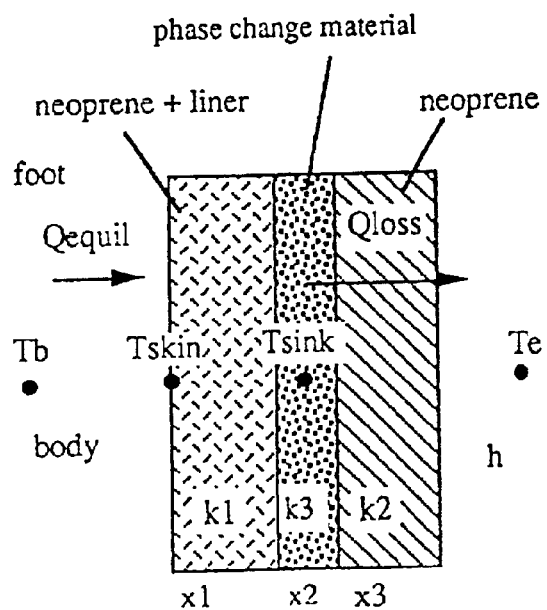
FIG. 17 shows a cross section of a phase change material thermal capacitor wet or dry suit.

An example of a thermal capacitor diving suit cross section is illustrated in FIG. 17. For this example, the same diving suit of FIG. 16 has been used, however, integral to the diving suit is a layer of phase change material, enclosed or encapsulated in an impermeable membrane, that acts as a thermal capacitor. The phase change material can be any paraffin, salt, crystalline, etc. material the undergoes a phase transition at a temperature appropriate to maintain thermal comfort and at a temperature compatible with regeneration in an environment consistent with its use. The phase change material layer might be interspersed with highly conductive metallic fibers to improve heat distribution throughout this layer. The capacitor serves two purposes. The first is to maintain thermal equilibrium and, hence, continuous thermal comfort. The second is to act as a thermal barrier or buffer to maintain this thermal equilibrium, for extended periods, regardless of changes in the external environment.

The maintenance of thermal equilibrium is accomplished in the following manner. A phase change material is chosen such that, given its melt point and the heat transfer coefficient between the skin and its melt line, $Q_{equil}$ can be attained according to equation [2], below. Depending upon the relative magnitude of contact conductance between the suit and the skin, this thermal resistance can be added as well.

$$Q_{equil} = \left[\frac{1}{\frac{x_1}{k_1 A} + \frac{0.5 x_2}{k_3 A}}\right](T_{skin} - T_{sink}) \qquad [2]$$

$Q_{equil}$ is maintained fairly constant as long as the phase change material is undergoing a phase transition, either from solid to liquid or liquid to solid. This simplification has been used to illustrate the buffering effect. Time variant analysis offer a more rigorous solution. Several analytical techniques have been developed to describe the change of phase heat transfer process. A rigorous, time variant solution to the PCM heat transfer process is given in "Numerical Simulation of a Latent Heat Exchanger," by J. Sun and C. K. Rush in Advances in Phase Change Heat Transfer.

The function of the phase change material as a barrier or buffer evolves from the characteristic of a phase change process. As a phase change material undergoes a phase transition, depending upon its initial state, it can either absorb or emit a quantity of heat equal to its latent heat of fusion while still maintaining a constant temperature. In such a manner, heat can be lost or gained from either side of this barrier, yet the temperature at this barrier will remain constant. This remains true until all of the phase change material has either solidified or liquefied. After this point, all of the latent capacity of the phase change material has been consumed and a sensible change in temperature results. The phase change material then acts as any other insulation and a gradual and continuous loss or addition of heat and, hence, rise or decline in temperature of the body results.

The result of this phase change material as a capacitor is that, in the ideal sense of continuous coverage, the heat transfer dynamics between the environment and this barrier and the heat transfer dynamics especially designed for thermal comfort inside this barrier have been de coupled. The quantities of phase change material required to maintain this de coupling is the mass whose equivalent heat of fusion equals the difference between the average $Q_{loss}$, and $Q_{equil}$ for the time period and environmental limits considered.

Again refer to the simplification of the steady state heat transfer process description of FIG. 2. Suppose that the same original lay-up is retained, however, a ⅛" layer of a hypothetical phase change material with a melting point equal to 71 F and a heat of fusion equal to 104 B/lbm has been added to constitute this thermal capacitor. Again, for example purposes only, suppose that the following conditions are true:

$h_f$=104 B/lbm
$T_{sink}$=71 F
$T_{skin}$=90 F
$T_{e1}$=43 F
$T_{e2}$=33 F
$x_1$=3/16"
$x_2$=1/8"
$x_3$=3/16"
$k_1$=0.03 B/hr-ft-F
$k_2$=0.02 B/hr-ft-F
$k_3$=0.2 B/hr-ft-F
h=150 B/hr-ft²-F
$A_f$=18 ft²
$C_{pf}$=0.83 B/lbm-F
$Q_{equil}$=625 B/hr From equation [2] it can be shown that the desired $Q_{equil}$ is indeed attained. As $Q_{equil}$ serves to induce a solid to liquid phase transition of the phase change material, the heat flow from the opposite side of this barrier or buffer to the external environment, $Q_{loss}$, simultaneously serves to induce a liquid to solid phase change. $Q_{loss}$ is estimated from equation [3].

$$Q_{loss} = \left[\frac{1}{\frac{0.5 x_2}{k_3 A} + \frac{x_3}{k_2 A} + \frac{1}{hA}}\right](T_{sink} - T_e) \qquad [3]$$

For Te₂=43 F, $Q_{loss}$=619 B/hr and for $T_{a1}$ 33 F, $Q_{loss}$=840 B/hr. Regardless of the change in external environment and $Q_{loss}$, $Q_{equil}$ will be maintained as long as sufficient thermal capacitance of the phase change material is provided. Finally, the quantity of phase change material required to maintain this de coupling with the environment, assuming Te2 33F and a 21 5 B/hr delta between $Q_{equil}$ and $Q_{loss}$ is computed by equation [4] to be equivalent to 2 lbm/hr.

$$\text{mass} = \frac{(Q_{loss} - Q_{equil}) t}{h_f} \qquad [4]$$

Since the thermal capacity of this ⅛" layer is 840 B and the de coupling requires 215 B/hr capacitance, continuous thermal equilibrium and comfort is maintained for close to four hours (for comparison, this same change of environments for the traditional diving suit resulted in a 1.5 F/hr drop in body core temperature of a 150 lbm individual). After this point, the wax must be warmed and regenerated to its liquid state to maintain this same thermal equilibrium. If not, the thermal performance will simply reduce to that of the traditional diving suit where $Q_{loss}$ is defined as in equation [1] with the additional resistance of the phase change material layer.

Intelligent choices of phase change melt points and lay-ups can be made such that regeneration can be accomplished by exposing the capacitor to a warm beach, to a high solar flux environment or to a room temperature environment. In order to minimize mass, it is desirable to choose the insulation values and thicknesses as well as phase change melt temperatures so that $Q_{equil}$ is achieved while minimizing $Q_{loss}$. An active, yet still simple, alternative procedure for regeneration might be the use of a hand dryer or portable heat source.

This same philosophy can be applied to ski boots, work boots, shoes, socks, shoe liners, garment liners, face masks, etc. The lay-up, dimensions, phase change material and properties were chosen for illustrative purposes to demonstrate the advantage in a diving suit. Obviously, variations on this concept are limitless and larger environmental envelopes must be considered as a lay-up and design is optimized.

Example 2

Thermal Capacitor Ski or Sport Boot

A simplification of the heat transfer process in a prior art ski boot is shown in FIG. 16. The term, $Q_{equil}$, refers to the amount of heat generated from the foot such that, if removed, no uncomfortable or medically unsafe net heat storage or loss in the foot results. Hence, thermal comfort is maintained. The term, $Q_{loss}$, refers to the amount of heat lost from the foot, through the boot and to the external environment. When $Q_{equil}$, or the amount of heat desirable to remove, is less than $Q_{loss}$, chilling of the foot occurs and vice versa.

For example purposes only, suppose that the following conditions are true:

$T_{skin}$=83.5 F
$T_{e1}$=15 F
$T_{e2}$=5 F
$x_1$=3/16"
$x_2$=1"
$k_1$=0.035 B/hr-ft-F
$k_2$=0.05 B/hr-ft-F
h=30 B/hr-ft²-F
$A_f$=0.67 ft²
$C_{pf}$=0.83 B/lbm-F
$Q_{equil}$=19.9 B/hr From these givens, one can compute $Q_{loss}$ according to equation [5], below, to be equal to 21.4 B/hr in a 15 F environment and 24.5 B/hr in a 5F environment. If one assumes no distribution of heat via the bloodstream, local chilling of the foot results and one can conservatively estimate a drop in temperature equal to 2 F/hr for the first case and 6.3 F/hr for the latter. Although this is less likely the case, had $Q_{equil}$ exceeded $Q_{loss}$, a rise in foot temperature would occur with a tendency towards overheating.

$$Q_{loss} = \left[\frac{1}{\frac{x_1}{k_1 A} + \frac{x_2}{k_2 A} + \frac{1}{hA}}\right](T_{skin} - T_e) \quad [5]$$

The disadvantage of the current practice to strictly use insulation for thermal control is that the thermal resistance is fixed in the boot. As explained above, to avoid overheating or chilling, i.e. thermal discomfort, a balance must be achieved between the heat generated in the foot, $Q_{equil}$, and the heat flow out of the foot, $Q_{loss}$. Since environmental conditions change constantly and since thermal conditions of the foot are directly linked to the changing environment through this fixed heat transfer path, no latitude exists to achieve this balance at conditions other than those at the single environment for which a solution exists.

Figure 18:
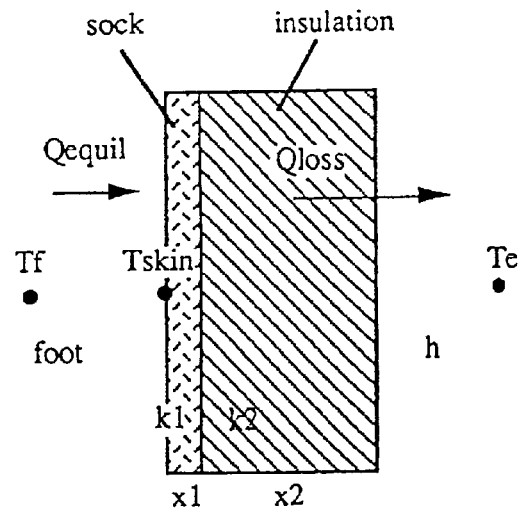
FIG. 18 shows a cross section of prior art traditional ski boot.
Figure 19:
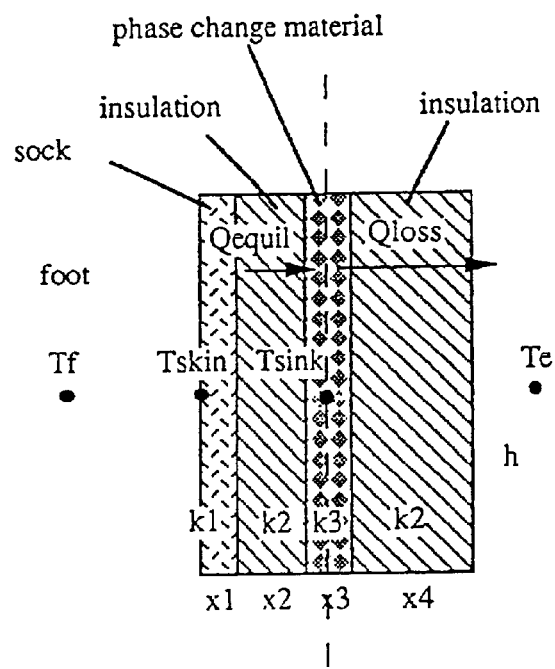
FIG. 19 shows a cross section of a phase change material thermal capacitor boot.

An example of a thermal capacitor ski boot cross section is illustrated in FIG. 19. For this example, the same boot of FIG. 18 has been used, however, integral to the boot is a layer of phase change material, enclosed or encapsulated in an impermeable membrane, that acts as a thermal capacitor. The phase change material can be any paraffin, salt, crystalline, etc. material the undergoes a phase transition at a temperature appropriate to maintain thermal comfort and at a temperature compatible with regeneration in an environment consistent with its use. The phase change material layer might be interspersed with highly conductive metallic fibers to improve heat distribution throughout this layer. The capacitor serves two purposes. The first is to maintain thermal equilibrium and, hence, continuous thermal comfort. The second is to act as a thermal barrier or buffer to maintain this thermal equilibrium, for extended periods, regardless of changes in the external environment.

The maintenance of thermal equilibrium is accomplished in the following manner. A phase change material is chosen such that, given its melt point and the heat transfer coefficient between the skin and its melt line, $Q_{equil}$ can be attained according to equation [6], below.

$$Q_{equil} = \left[\frac{1}{\frac{x_1}{k_1 A} + \frac{x_2}{k_2 A} + \frac{0.5 x_3}{k_3 A}}\right](T_{skin} - T_{sink}) \quad [6]$$

$Q_{equil}$ is maintained fairly constant as long as the phase change material is undergoing a phase transition, either from solid to liquid or liquid to solid.

The function of the phase change material as a barrier or buffer evolves from the characteristic of a phase change process. As a phase change material undergoes a phase transition, depending upon its initial state, it can either absorb or emit a quantity of heat equal to its latent heat of fusion while still maintaining a constant temperature. In such a manner, heat can be lost or gained from either side of this barrier, yet the temperature at this barrier will remain constant. This remains true until all of the phase change material has either solidified or liquefied. After this point, all of the latent capacity of the phase change material has been consumed and a sensible change in temperature results. The phase change material then acts as any other insulation and a gradual and continuous loss or addition of heat and, hence, rise or decline in temperature of the foot results.

The result of this phase change material as a capacitor is that the heat transfer dynamics between the environment and this barrier and the heat transfer dynamics especially designed for thermal comfort inside this barrier have been de coupled. The quantities of phase change material required to maintain this decoupling is the mass whose equivalent heat of fusion equals the difference between the average $Q_{loss}$ and $Q_{equil}$ for the time period and environmental limits considered.

Again refer to the simplified description of FIG. 18. Suppose that the same original lay-up is retained, however, a ¼" layer of a hypothetical phase change material with a melting point equal to 50 F and a heat of fusion equal to 105 B/lbm has been added to constitute this thermal capacitor. Again, for example purposes only, suppose that the following conditions are true:

$h_f$=105 B/lbm
$T_{sink}$=50 F
$T_{skin}$=83.5 F
$T_{e1}$=15 F
$T_{e2}$=5 F
$x_1$=3/16"
$x_2$=3/8"
$x_3$=¼"

$x_4 = 5/8''$
$k_1 = 0.035$ B/hr-ft-F
$k_2 = 0.05$ B/hr-ft-F
$k_3 = 0.2$ B/hr-ft-F
$h = 30$ B/hr-ft$^2$-F
$A_f = 0.67$ ft$^2$
$C_{pf} = 0.83$ B/lbm-F
$Q_{equil} = 19.9$ B/hr From equation [6] it can be shown that the desired $Q_{equil}$ is indeed attained. As $Q_{equil}$ serves to induce a solid to liquid phase transition of the phase change material, the heat flow from the opposite side of this barrier or buffer to the external environment, $Q_{loss}$, simultaneously serves to induce a liquid to solid phase change. $Q_{loss}$ is estimated from equation [7].

$$Q_{loss} = \left[\frac{1}{\frac{0.5x_3}{k_3 A} + \frac{x_4}{k_2 A} + \frac{1}{hA}}\right](T_{sink} - T_e) \quad [7]$$

For $T_{e1} = 15$ F, $Q_{loss} = 20.8$ B/hr and for $T_{e2}$ 5 F, $Q_{loss} = 26.7$ B/hr. Regardless of the change in external environment and $Q_{loss}$, $Q_{equil}$ will be maintained as long as sufficient thermal capacitance of the phase change material is provided. Finally, the quantity of phase change material required to maintain this de coupling with the environment, based on the extreme chosen, is computed by equation [8]. Assuming Te=5F and a 6.8 B/hr delta between $Q_{equil}$ and $Q_{loss}$, this mass is computed to be less than 0.1 lbm per hour.

$$\text{mass} = \frac{(Q_{loss} - Q_{equil})t}{h_f} \quad [8]$$

Since the thermal capacity of this ¼" layer is 63 B, continuous thermal equilibrium and comfort is maintained for up to nine hours (for comparison, this same change of environments for the traditional boot resulted in an increase in the temperature drop of the foot from 2 F/hr to 6.3 F/hr). After this point, the wax must be warmed and regenerated to its liquid state to maintain this same thermal equilibrium. If not, the thermal performance will simply reduce to that of the traditional ski boots where $Q_{loss}$ is defined as in equation [5] with the additional resistance of the phase change material layer.

Intelligent choices of phase change melt points and lay-ups can be made such that regeneration can be accomplished by exposing the capacitor to a room temperature environment. An active, yet still simple, alternative procedure for regeneration might be the use of a hand dryer.

Thus, the invention offers a simple, reliable solution to the "cold feet" problem, whether it is applied to ski boots, work boots, shoes, socks, liners, etc. The lay-up, dimensions, phase change material and properties were chosen for illustrative purposes to demonstrate the advantage of such a boot. Obviously, variations on this concept are limitless and larger environmental envelopes must be considered as a lay-up and design is optimized.

Applications of the Flexible PCM Composite

Figure 13:
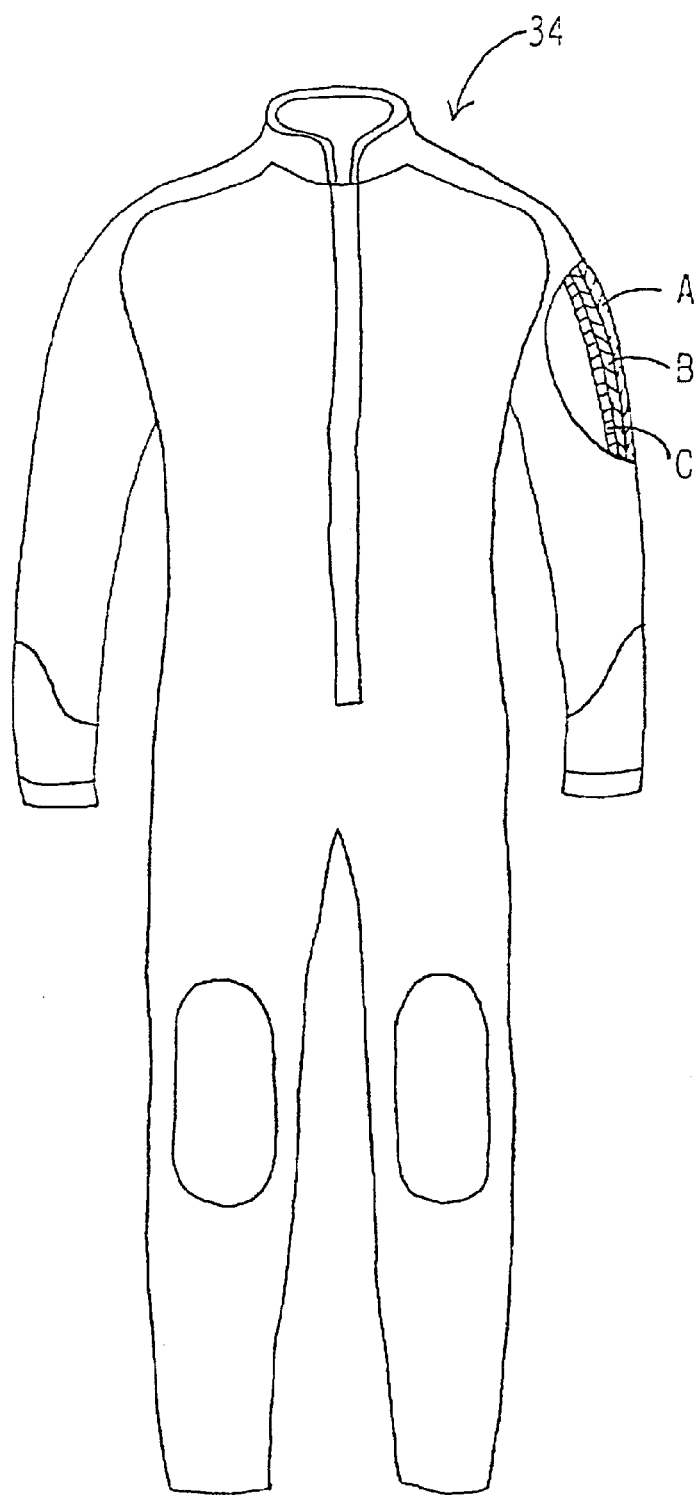
FIG. 13 shows a diver's wet suit made with the flexible PCM composite.

FIG. 13 shows a diver's exposure suit 34, commonly called a wet suit, made in accordance with the present invention. One of the inherent problems in underwater diving is that water has such a high heat transfer coefficient and a high heat capacity that it draws heat out of the body very quickly. Even in tropical waters most divers have to wear an insulative exposure suit to prevent hypothermia. For some divers, however, an insulative wetsuit is not enough because they do not generate enough body heat to compensate for the heat loss to the surrounding water. In colder waters, even the hardiest divers must resort to expensive and complicated drysuits to prevent hypothermia.

Accordingly, this embodiment of the present invention takes the form of a diver's wetsuit made with the flexible PCM composite so that it provides the diver with a reservoir of heat to keep warm while diving. By way of example, the wetsuit shown is made of a material analogous to the three layer PCM composite in FIGS. 2 and 4. The preferred matrix material is closed cell neoprene foam. There is an insulative outer layer A of the matrix material alone. The middle layer B has a high concentration of PCM as pellets or capsules. There is a thin inner layer C of the matrix material so that there is a good thermal coupling between the PCM and the wearer's skin.

For mild water temperatures the PCM chosen can be a buffering PCM with a transition temperature between normal skin temperature and the water temperature. The buffering PCM does not reverse the heat flow from the body, but only slows it down to a normal level, so that the person remains warmer in the water longer. The amount of PCM can be chosen so that the thermal mass is enough to act as a buffer for the duration of a normal dive, which seldom exceeds an hour for recreational divers.

Using a buffering PCM has an added benefit when diving in mild temperatures. When using a standard insulative wetsuit, upon resurfacing, a diver will quickly have to strip off the wetsuit to avoid overheating. A wetsuit with enough insulation to keep a diver warm in the water has much too much insulation for wearing in air. With the buffering PCM, however, when the skin temperature rises, it will start to melt the solidified PCM, regenerating the PCM for the next dive and protecting the wearer from overheating. Thus, the buffering action of the PCM protects the wearer from the extremes of high and low environmental temperatures. The buffering PCM can also be regenerated by taking the wetsuit indoors or putting it in a warm car until the next dive.

For diving in cold water or for divers who always have trouble keeping warm, the composite can be made with a heating PCM. The PCM is chosen with a transition temperature above the skin temperature or even above body core temperature. Thus, the heat flow is reversed so that the PCM gives up heat to the body to compensate for the heat loss to the water from exposed skin. If the transition temperature is high enough to be beyond the comfort range for skin contact, the inner layer C should be thickened to regulate the heat flow between the PCM and the skin.

It is even conceivable that a wetsuit with a cooling PCM would be useful for the rare occasion when someone would be diving in very warm water such as a hot spring.

Figure 14:
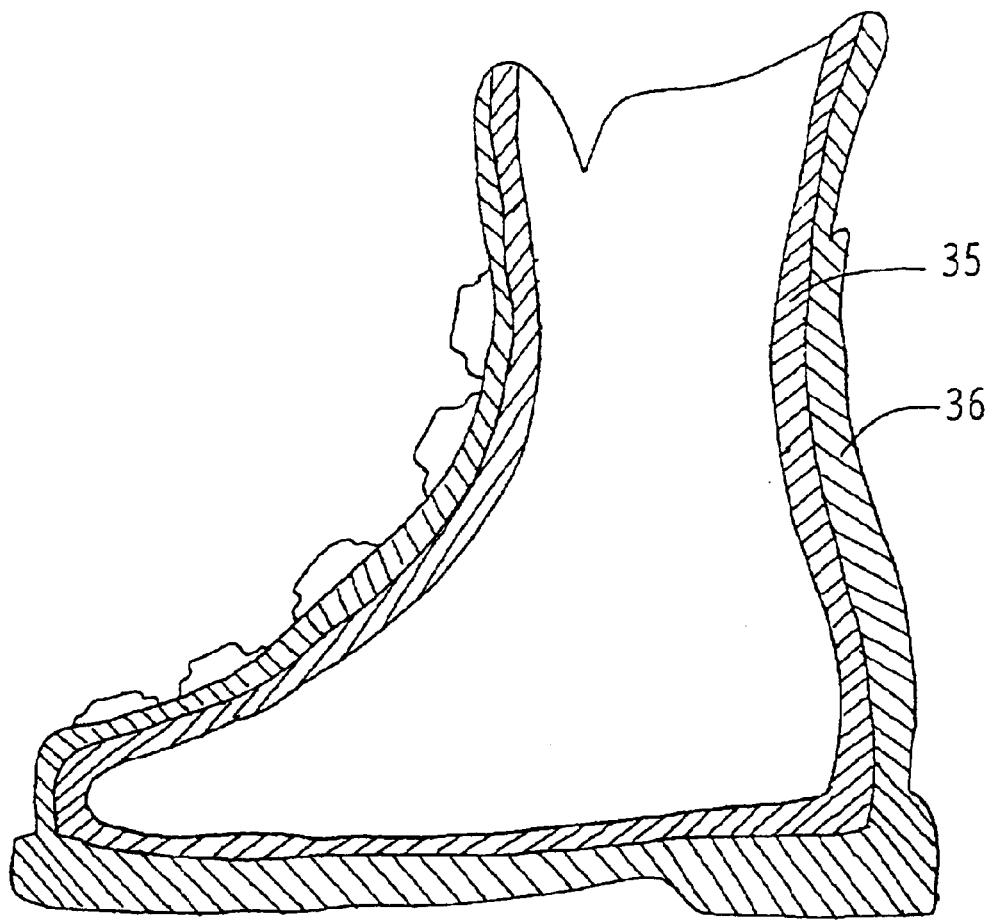
FIG. 14 shows a ski boot liner made with the flexible PCM composite.

Another application of the flexible PCM Composite is for cold weather wear. Again, a buffering PCM or a heating PCM can be chosen depending on the temperature extremes and the duration of use. Examples of cold weather wear that can benefit from the use of the flexible PCM composite are hats, socks, gloves, mittens, ski masks, and ski boot liners. FIG. 14 shows a cross section of a modern downhill ski boot 36 to which has been added a flexible PCM composite inner liner 35. The liner may be a permanent part of the boot or it may be made removable so that an already regenerated liner can be slipped into the boot between downhill runs. This design is equally applicable to crosscountry ski boots, snowmobile boots and winter hiking boots. The flexibility of the PCM composite makes it far superior in this application to any of the prior art warming devices that use an inflexible PCM salt for heat storage.

Figure 15:
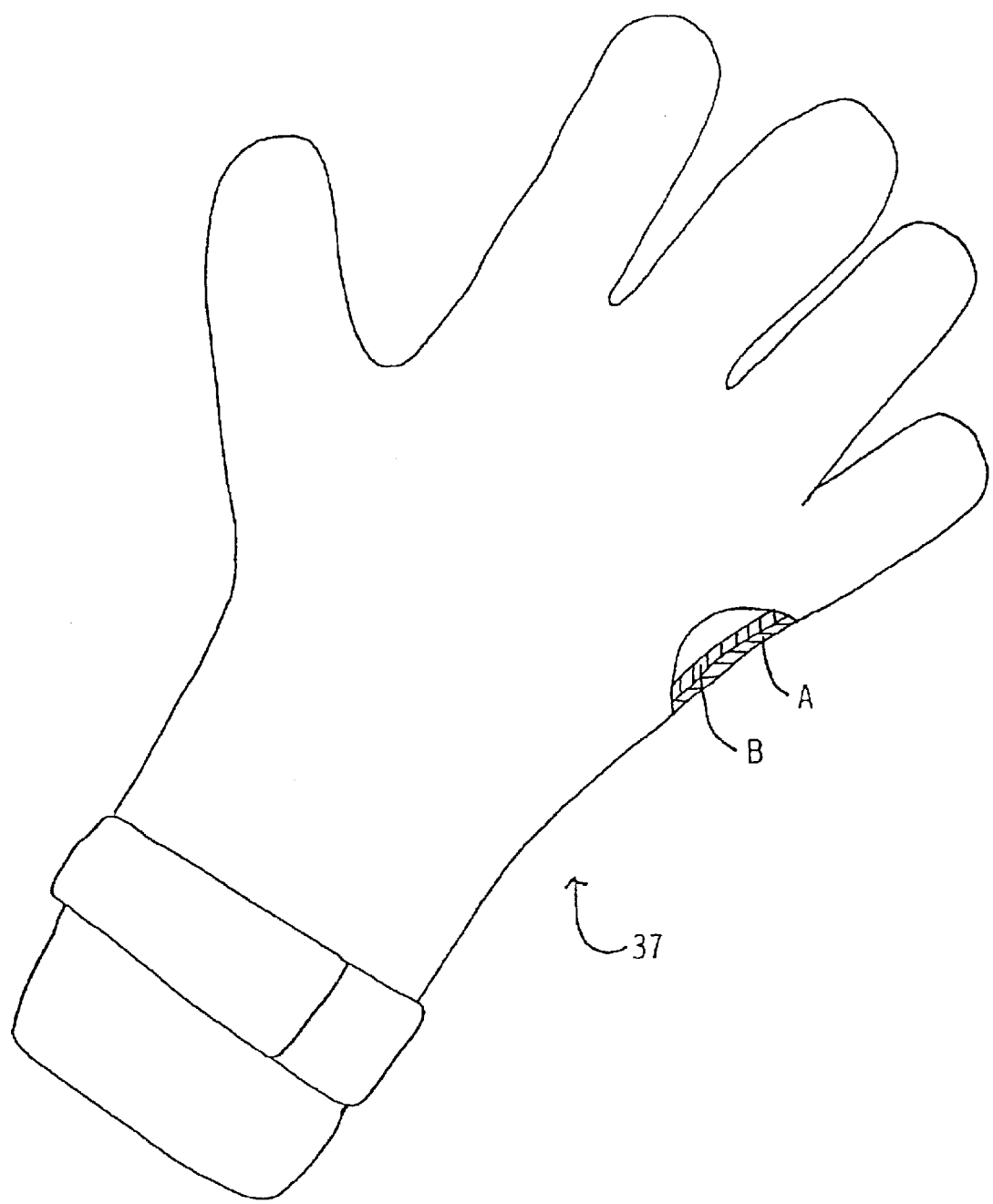
FIG. 15 shows a glove made with the flexible PCM composite.

FIG. 15 shows a glove 37 that has been made with a two layer flexible PCM composite. Layer A is an outer insulating layer and layer B is the PCM-containing inner layer. The glove can be made with a closed cell polymer foam matrix for underwater use or with a breathable open cell foam for cold weather wear.

Another area of application of the flexible PCM composite is for therapeutic medical products. One example is a therapeutic blanket made of a flexible PCM composite in accordance with the present invention. If made with a cooling PCM having a transition temperature below normal skin temperature, such a blanket could be used for cooling febrile patients in a careful and controlled manner. It would not require frequently repeated applications the way alcohol baths do, and by careful choice of the PCM transition temperature it would avoid the danger of overcooling the patient that is inherent with ice packs. Alternatively, a heating PCM can be used to make a blanket that is useful for gently and controllably reheating hypothermia patients.

Another therapeutic medical use of the flexible PCM composite is to incorporate it into elastic wraps or orthopedic joint supports. Thus hot or cold therapy can be combined with a supporting bandage for joints or muscles. Another medical use envisioned for the flexible PCM composite is to incorporate it into an artificial skin that can be used for protection of wounds from infection while simultaneously applying hot or cold therapy. A nonstick inner surface can be added to the composite for this application so that it does not adhere to the wound.

The flexible PCM composite of the present invention will also find a great many other uses in everyday items. For instance flexible containers can be made using a cooling PCM to keep perishable foods or other material cold.

Although the examples given include many specificities, they are intended as illustrative of only one possible embodiment of the invention. Other embodiments and modifications will, no doubt, occur to those skilled in the art. Thus, the examples given should only be interpreted as illustrations of some of the preferred embodiments of the invention, and the full scope of the invention should be determined by the appended claims and their legal equivalents.

TABLE 1

| Phase Change Material | Transition Temperature ° F. | Transition Temperature ° C. | Latent Heat (Btu/lbm) | NOTES |
|---|---|---|---|---|
| Glycerol | 64.8 | 18.2 | 86.3 | non-paraffin organic |
| Acetic Acid | 62 | 16.7 | 82.6 | non-paraffin organic |
| Polyethylene Glycol 600 | 68–77 | | 63 | non-parrafin organic |
| Camphene | 50 | 10 | 102 | non-paraffin |
| Oxasoline Wax | 122 | 50 | | non-paraffin |
| d-Lactic Acid | 79 | 26.1 | 79 | non-paraffin organic |
| formic acid | 47 | 8.3 | 118 | organic |
| acrylic acid | 54 | 12.2 | 66.7 | organic |
| p-Xylene | 56 | 13.3 | 68.1 | organic |
| caprylic acid | 61 | 16.1 | 63.7 | organic |
| Jojoba Wax | 52–53.2 | 11.2–11.8 | | insoluble fatty acids of natural oils and waxes |
| Cotton Seed Oil | 94.1 | 34.5 | | insoluble fatty acids of natural oils and waxes |
| Coconut | 77 | 25 | | insoluble fatty acids of natural oils and waxes |
| Almond | 56.3 | 13.5 | | insoluble fatty acids of natural oils and waxes |
| Beechnut | 74.3 | 23.5 | | insoluble fatty acids of natural oils and waxes |
| Black Mustard | 61.7 | 16.5 | | insoluble fatty acids of natural oils and waxes |
| Candlenut | 68.9 | 20.5 | | insoluble fatty acids of natural oils and waxes |
| Castor Oil | 55.4 | 13 | | insoluble fatty acids of natural oils and waxes |
| Corn Oil | 65.3 | 18.5 | | insoluble fatty acids of natural oils and waxes |
| Cotton Seed Stearin | 83.3 | 28.5 | | insoluble fatty acids of natural oils and waxes |
| Esparto | 63.5 | 17.5 | | insoluble fatty acids of natural oils and waxes |
| Poppy Seed | 68.9 | 20.5 | | insoluble fatty acids of natural oils and waxes |
| Rape Seed (Canola) | 66.2 | 19 | | insoluble fatty acids of natural oils and waxes |
| Pumpkin Seed | 136.4 | 58 | | insoluble fatty acids of natural oils and waxes |
| Soy Bean | 80.6 | 27 | | insoluble fatty acids of natural oils and waxes |
| Sunflower | 73.4 | 23 | | insoluble fatty acids of natural oils and waxes |
| Walnut | 57.74 | 14.3 | | insoluble fatty acids of natural oils and waxes |
| White Mustard Seed | 59.9 | 15.5 | | insoluble fatty acids of natural oils and waxes |
| Beeswax | 143 | 62 | 76 | insoluble fatty acids of natural oils and waxes |
| NH4Cl.Na2SO4.10H2O | 52 | 11.1 | 70 | hydration-dehydration reaction |
| NaCl.NH4Cl.2NaSO42.20H2O | 55 | 12.8 | 78 | hydration-dehydration reaction |
| NaCl.Na2.SO4.10H2O | 65 | 18.3 | 80 | hydration-dehydration reaction |
| n-tetradecane | 41.9 | 5.5 | 98 | hydrocarbon paraffins |
| n-pentadecane | 50 | 10 | 88 | hydrocarbon paraffins |
| n-hexadecane | 62.1 | 16.7 | 102 | hydrocarbon paraffins |
| n-heptadecane | 71.1 | 21.7 | 92 | hydrocarbon paraffins |
| n-octadecane | 82.4 | 28 | 105 | hydrocarbon paraffins |
| n-nanodecane | 89.6 | 32 | | hydrocarbon paraffins |
| n-eicosane | 98.1 | 36.7 | 106 | hydrocarbon paraffins |
| n-heneicosane | 104.4 | 40.2 | 86 | hydrocarbon paraffins |
| n-decosane | 111.2 | 44 | 107 | hydrocarbon paraffins |
| n-tricosane | 117.5 | 47.5 | 100 | hydrocarbon paraffins |
| Trimethyolethane | 178 | 81 | | mesocrystalline phase change |
| Neopentyl Glycol | | 42 | | mesocrystalline phase change |
| lithium chloride | | | | |
| calcium chloride hydrate | | | | |
| 1-decanol octadecane | | | | |

TABLE 1-continued

| Phase Change Material | Transition Temperature °F. | Transition Temperature °C. | Latent Heat (Btu/lbm) | NOTES |
|---|---|---|---|---|
| C-16 to C-22 alkyl hydrocarbons | | 10 to 50 | >50 | alkyl hydrocarbon |
| natural rubber | | varies to 25 | | crystalline phase change |
| polychloropropene | | 32 | | |
| Witco 45A | | 31 | >54 | crystalline alkyl hydrocarbons |
| Witco K-61 | | 24 | >54 | crystalline alkyl hydrocarbons |
| Witco K-51 | | 17 | >54 | crystalline alkyl hydrocarbons |
| Witco 85010-1 | | 7 | >54 | crystalline alkyl hydrocarbons |
| pentaerythritol | | plastic crystals (no change of state but release high amounts of E before melting) | | |
| polyhydric alcohols | | plastic crystals (no change of state but release high amounts of E before melting) | | |
| acrylate and methacrylate polymers | | −17.8 | | with C-16 to C-18 alkyl side chains |
| CaBr2.6H20/NaCl | 59 | 15 | | hydration-dehydration reaction |
| Na2SO4.10H2O/NaCl | 64 | 17.8 | | hydration-dehydration reaction |
| CaCl2.6H2O | 82 | 27.8 | | hydration-dehydration reaction |
| Na2SO4.10H2O | 90 | 32.2 | | hydration-dehydration reaction |
| CaBr2.6H20 | 93 | 33.9 | | hydration-dehydration reaction |

I claim:

1. A garment or material thereof for metabolic cooling and for insulation of a user in at least a cold ambient environment below a phase transition temperature of a thermal storage material, comprising:
   a buffering thermal storage material capable of storing thermal energy as the latent heat of phase change located in the garment or material thereof;
   said thermal storage material comprising a phase change material having at least one actual phase transition temperature between 41.9 and 80.6 degrees Fahrenheit; and
   said thermal storage material having a thermal mass of the phase change material at least equivalent to a thermal loading of the phase change material of 13.5 to 1120.08 BTU per cubic foot of the garment or material thereof.

2. The garment or material thereof of claim 1, wherein:
   said thermal storage material comprises a mixture of at least two phase change materials having at least two different transition temperatures; or
   said thermal storage material comprises at least two layers of phase change materials with different transition temperatures.

3. The garment or material thereof of claim 1, wherein said phase change material undergoes a solid-solid transition or a solid-liquid transition.

4. The garment or material thereof of claim 1, wherein said thermal storage material comprises a phase change material absorbed in particles of a superabsorbent material.

5. The garment or material thereof of claim 1, wherein said phase change material is micro encapsulated.

6. The garment or material thereof of claim 1, wherein said phase change material is encapsulated.

7. The garment or material thereof of claim 1, wherein said phase change material is in pellets.

8. The garment or material thereof of claim 1, wherein said phase change material is contained in a cellulose matrix.

9. The garment or material thereof of claim 1, further comprising a thermal control layer located on a first side of said thermal storage material adapted to face a wearer and an insulative layer located on a second side of said thermal storage material adapted to face the ambient environment, said insulative layer being of greater insulative value than said thermal control layer.

10. The garment or material thereof of claim 9, wherein the insulative layer comprises a semipermeable membrane which is permeable to water vapor but impermeable to liquid water.

11. The garment or material thereof of claim 1, wherein said garment comprises an article of clothing.

12. The garment or material thereof of claim 11, wherein said article of clothing is selected from the group consisting of a shirt, a jacket, trousers, a blanket, a gaiter, a facial mask, a hat and an earmuff.

13. The garment or material thereof of claim 11, wherein said article of clothing is in the form of a removable liner configured to be worn in combination with other clothing.

14. The garment or material thereof of claim 11, wherein said article of clothing comprises a diver's wetsuit.

15. The garment or material thereof of claim 11, wherein said thermal storage material is contained within closed internal spaces of the article of clothing or is incorporated into a fabric of the article of clothing.

16. The garment or material thereof of claim 1, wherein said garment comprises an article of footwear.

17. The garment or material thereof of claim 16, wherein said article of footwear comprises a ski boot.

18. The garment or material thereof of claim 16, wherein said article of footwear comprises a shoe.

19. The garment or material thereof of claim 16, wherein said article of footwear comprises a ski boot liner, a sock or a removable liner configured to be worn in combination with other footwear.

20. The garment or material thereof of claim 16, wherein said phase change material is enclosed in internal spaces within said footwear.

21. The garment or material thereof of claim 1, wherein said phase change material comprises an organic material.

22. The garment or material thereof of claim 1, wherein at least one said phase change material has an actual phase transition temperature in a range from 41.9 degrees Fahrenheit to 71.1 degrees Fahrenheit.

23. The garment or material thereof of claim 1, wherein said phase change material comprises an organic material.

24. An article of footwear for metabolic cooling and for insulation of a user in at least a cold ambient environment below a phase transition temperature of a thermal storage material, comprising:
   a buffering thermal storage material capable of storing thermal energy as a latent heat of phase change located in the article of footwear;
   said thermal storage material comprising a phase change material having at least one actual phase transition temperature between 41.9 and 80.6 degrees Fahrenheit; and said thermal storage material having a thermal mass of the phase change material at least equivalent to a thermal loading of the phase change material of 13.5 to 1120.08 BTU per cubic foot of the article.

25. A garment or material thereof for metabolic cooling and for insulation of a user in at least a cold ambient environment below a phase transition temperature of a thermal storage material, comprising:

a buffering thermal storage material capable of storing thermal energy as the latent heat of phase change located in the garment or material thereof;

said thermal storage material comprising a phase change material having at least one actual phase transition temperature between 41.9 and 80.6 degrees Fahrenheit; and said thermal storage material has a thermal loading of phase change material from 1.34 BTU to 10.3 BTU per square foot of a surface area of the garment or material thereof.

26. The garment or material thereof of claim 25, wherein:
at least one phase change material has an actual phase transition temperature in a range from 41.9 degrees Fahrenheit to 71.1 degrees Fahrenheit.

27. The garment or material thereof of claim 25, wherein the thermal storage material comprises an aggregate of phase change material particles incorporated into a bonding material.

28. The garment or material thereof of claim 25, wherein the thermal storage material comprises a dispersion of a phase change material in a coating material.

29. The garment or material thereof of claim 25, wherein the thermal storage material comprises a dispersion of a phase change material that was incorporated into a paste while in a liquid state during lamination.

30. The garment or material thereof of claim 25, further comprising a wicking element located in the garment or material thereof.

31. An article of bedding for metabolic cooling and for insulation of a user in an ambient environment, comprising:

a buffering thermal storage material capable of storing thermal energy as the latent heat of phase change located in the article;

said thermal storage material comprising a phase change material having at least one actual phase transition temperature between 41.9 and 80.6 degrees Fahrenheit; and said thermal storage material has a thermal loading of phase change material from 1.34 BTU to 10.3 BTU per square foot of a surface area of the article.

32. The article of claim 31, wherein:
at least one phase change material has an actual phase transition temperature in a range from 41.9 degrees Fahrenheit to 71.1 degrees Fahrenheit.

33. A garment or material thereof for metabolic cooling and for insulation of a user in at least a cold ambient environment below a phase transition temperature of a thermal storage material, comprising:

a buffering thermal storage material capable of storing thermal energy as the latent heat of phase change located in the garment or material thereof;

said thermal storage material comprising a phase change material having at least one actual phase transition temperature between 41.9 and 80.6 degrees Fahrenheit; and said thermal storage material having a thermal loading of the phase change material of 13.5 BTU to 104.08 BTU per cubic foot of the garment or material thereof.

34. A garment or material thereof for metabolic cooling for insulation of a user in at least a cold ambient environment below a phase transition temperature of a thermal storage material, comprising:

a buffering thermal storage material capable of storing thermal energy as the latent heat of phase change located in the garment or material thereof;

said thermal storage material comprising a phase change material having at least one actual phase transition temperature between 41.9 and 80.6 degrees Fahrenheit; and said thermal storage material having a thermal loading of the phase change material of 104.08 BTU to 784.7 BTU per cubic foot of the garment or material thereof.

35. The garment or material thereof of claim 34, wherein the thermal storage material has a thermal loading of the phase change material of 300.13 BTU 784.7 BTU per cubic foot of the garment or material thereof.

36. The garment or material thereof of claim 34, wherein the thermal storage material has a thermal loading of the phase change material of 104.08 BTU to 300.13 BTU per cubic foot of the garment or material thereof.

37. A garment or material thereof for metabolic cooling and for insulation of a user in at least a cold ambient environment below a phase transition temperature of a thermal storage material, comprising:

a buffering thermal storage material capable of storing thermal energy as the latent heat of phase change located in the garment or material thereof;

said thermal storage material comprising a phase change material having at least one actual phase transition temperature between 41.9 and 80.6 degrees Fahrenheit; and said thermal storage material having a thermal loading of the phase change material of 784.7 BTU to 1120.08 BTU per cubic foot of the garment or material thereof.

38. A garment or material thereof for metabolic cooling and for insulation of a user in at least a cold ambient environment below a phase transition temperature of a thermal storage material, comprising:

a buffering thermal storage material capable of storing thermal energy as the latent heat of phase change located in the garment or material thereof;

said thermal storage material comprising a phase change material having at least one actual phase transition temperature between 41.9 and 80.6 degrees Fahrenheit; and said thermal storage material having a thermal mass of the phase change material at least equivalent to a thermal loading of the phase change material of 13.5 BTU per cubic foot of the garment or material thereof; and said thermal storage material comprises at least two layers of phase change materials with different transition temperatures; and a transition temperature of an inner layer of said phase change material is greater than a transition temperature of an outer layer of said layer of phase change material which is adapted to be farther from a skin of the wearer than the inner layer.

39. An article comprising a garment, an article of bedding, or material thereof for metabolic cooling and for insulation of a user in at least a cold ambient environment below a phase transition temperature of a thermal storage material, comprising:

a buffering thermal storage material capable of storing thermal energy as the latent heat of phase change located in the article;

said thermal storage material comprising a phase change material having at least one actual phase transition temperature between 41.9 and 94.1 degrees Fahrenheit; and said thermal storage material has a thermal loading of phase change material from 1.34 BTU to 10.3 BTU per square foot of a surface area of the article.

40. The article of claim 39, wherein the article comprises an article of bedding.

41. The article of claim 39, wherein the article comprises a garment.

42. An article comprising a garment, an article of bedding, or material thereof for metabolic cooling and for insulation of a user in a cold ambient environment below a phase transition temperature of a thermal storage material, comprising:

a buffering thermal storage material capable of storing thermal energy as the latent heat of phase change located in the article;

said thermal storage material comprising a phase change material having at least one actual phase transition temperature between 41.9 and 94.1 degrees Fahrenheit; and said thermal storage material has a thermal loading of phase change material from 13.5 BTU to 1120.08 BTU per cubic foot of a surface area of the article.

43. The article of claim 42, wherein the article comprises an article of bedding.

44. The article of claim 42, wherein the article comprises a garment.

* * * * *